(12) United States Patent
Takeshita et al.

(10) Patent No.: US 8,859,242 B2
(45) Date of Patent: *Oct. 14, 2014

(54) METHOD FOR PRODUCING BASIC SUBSTANCE

(75) Inventors: Ryo Takeshita, Kawasaki (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/404,131

(22) Filed: Feb. 24, 2012

(65) Prior Publication Data

US 2012/0149072 A1   Jun. 14, 2012

Related U.S. Application Data

(60) Division of application No. 12/834,381, filed on Jul. 12, 2010, now Pat. No. 8,198,053, which is a division of application No. 11/697,794, filed on Apr. 9, 2007, now Pat. No. 7,790,422, which is a continuation of application No. PCT/JP2005/018657, filed on Oct. 7, 2005.

(30) Foreign Application Priority Data

Oct. 7, 2004   (JP) ................................ 2004-295123

(51) Int. Cl.
| | |
|---|---|
| *C12P 13/24* | (2006.01) |
| *C12P 13/10* | (2006.01) |
| *C12P 13/08* | (2006.01) |
| *C12P 13/04* | (2006.01) |
| *C12N 1/20* | (2006.01) |

(52) U.S. Cl.
CPC ................. *C12P 13/08* (2013.01); *C12P 13/24* (2013.01); *C12N 1/20* (2013.01); *C12P 13/10* (2013.01)
USPC ........... 435/107; 435/106; 435/114; 435/115; 435/252.8

(58) Field of Classification Search
None
See application file for complete search history.

(56) References Cited

U.S. PATENT DOCUMENTS

| | | | |
|---|---|---|---|
| 3,650,899 A | 3/1972 | Noguchi et al. | |
| 3,766,010 A | 10/1973 | Ikeda et al. | |
| 3,839,151 A | 10/1974 | Tanaka et al. | |
| 4,275,157 A | 6/1981 | Tosaka et al. | |
| 5,133,976 A | 7/1992 | Rouy | |
| 5,431,933 A | 7/1995 | Binder et al. | |
| 5,763,230 A | 6/1998 | De Hollander et al. | |
| 5,770,409 A | 6/1998 | Pfefferle et al. | |
| 5,840,358 A | 11/1998 | Höfler et al. | |
| 5,912,113 A | 6/1999 | Nakamura et al. | |
| 6,025,169 A | 2/2000 | Nakamura et al. | |
| 6,579,699 B1 | 6/2003 | Kikuchi et al. | |
| 6,878,533 B2 | 4/2005 | Tsujimoto et al. | |
| 6,905,819 B1 | 6/2005 | Matsuzaki et al. | |
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,160,704 B2 | 1/2007 | Takeshita et al. | |
| 7,192,747 B2 | 3/2007 | Ono et al. | |
| 7,192,748 B2 | 3/2007 | Usuda et al. | |
| 7,211,421 B2 | 5/2007 | Tsujimoto | |
| 7,220,570 B2 | 5/2007 | Usuda et al. | |
| 7,223,572 B1 | 5/2007 | Gunji et al. | |
| 7,244,569 B2 | 7/2007 | Matsuzaki et al. | |
| 7,468,262 B2 | 12/2008 | Usuda et al. | |
| 7,790,422 B2 | 9/2010 | Takeshita et al. | |
| 8,008,047 B2 | 8/2011 | Iyo et al. | |
| 2002/0025564 A1 | 2/2002 | Kobayashi et al. | |
| 2002/0153261 A1 | 10/2002 | Hasegawa et al. | |
| 2002/0155556 A1 | 10/2002 | Imaizumi et al. | |
| 2007/0249017 A1 | 10/2007 | Usuda et al. | |
| 2008/0038825 A1 | 2/2008 | Gunji et al. | |
| 2009/0215130 A1 | 8/2009 | Iyo et al. | |
| 2009/0258401 A1 | 10/2009 | Iyo et al. | |
| 2010/0273221 A1 | 10/2010 | Takeshita et al. | |
| 2011/0003347 A1 | 1/2011 | Takeshita et al. | |
| 2011/0281311 A1 | 11/2011 | Wakasa et al. | |

FOREIGN PATENT DOCUMENTS

| | | |
|---|---|---|
| CA | 2 078 364 | 3/1993 |
| DE | 290213 A5 | 5/1991 |
| EP | 0 532 867 | 3/1993 |
| EP | 0 809 940 | 12/1997 |
| EP | 0979876 A2 | 2/2000 |
| EP | 0979876 A3 | 2/2000 |
| GB | 1 244 717 | 9/1971 |
| JP | 54-86692 | 7/1979 |

OTHER PUBLICATIONS

Singer, M., et al., Genes & Genomes, Moscow, "MIR," 1998, v 1, Chapter 1.3.a.
International Preliminary Report on Patentability for PCT Patent App. No. PCT/JP2005/018657 (Apr. 19, 2007).

(Continued)

*Primary Examiner* — Suzanne M Noakes
*Assistant Examiner* — Jae W Lee
(74) *Attorney, Agent, or Firm* — Shelly Guest Cermak; Cermak Nakajima McGowan LLP

(57) ABSTRACT

A method for producing a basic substance by fermentation comprising culturing a microorganism having an ability to produce the basic substance in a liquid medium contained in a fermentation tank to produce and accumulate the basic substance in the medium, wherein amount of sulfate and/or chloride ions used as counter ions of the basic substance is reduced by adjusting total ammonia concentration in the medium to be within a specific concentration range during at least a part of the total period of culture process.

13 Claims, 6 Drawing Sheets

(56) References Cited

OTHER PUBLICATIONS

Office Action for Russian Patent App. No. 2007116981 (Feb. 6, 2008) with English translation.
Notice of Reason for Rejection for Japanese Patent App. No. 2006-539347 (Apr. 12, 2011) with English translation thereof.
Supplementary European Search Report for European Patent App. No. 05790247.0 (Sep. 19, 2011).
Third Party Observations under Art 115 EPC filed on Mar. 16, 2010 in the corresponding EP patent app. No. 05790247.0.
Opposition filed on Nov. 17, 2011 against the related EP patent app. No. 01120248.8, and English translation thereof.
Letter of the patent law firm Strehl Schübel-Hopf & Partner dated Jan. 3, 2008, together with enclosures.
Hirose Y., Biochemical Effects of Oxygen Supply and Carbon Dioxide Removal, in: Progress in Industrial Microbiology:Biotechnology of Amino Acid Production, Elsevier: vol. 24, p. 67-80, 1986.
Akashi et al., Journal of Fermentation Technology, "Inhibitory Effects of Carbon Dioxide and Oxygen in Amino Acid Fermentation," vol. 57, No. 4, p. 317-320, 1979.
Crueger and Crueger, Lehrbuch der Angewandten Mikrobiologie, Akademische Verlagsgesellschaft, Wiesbaden 1982, pp. 89-90.
Advances in Biotechnological Engineering Biotechnology, Springer-Verlag (2003); vol. 79; Preface by Robert Faurie and Jürgen Thommel; and Pfefferle et al., Biotechnological Manufacture of Lysine, p. 59-112.
Aida T. et al, Tohoku Journal of Agricultural Research, 11(4), p. 377-388, 1960.
Communication Pursuant to Rule 114(2) EPC from European Patent App. No. 05790247.0 (Jan. 2, 2014) with English translation of the relevant parts of the Communication.
Item D4 cited in the above Communication: Marx, A., "Bestimmung des Kohlenstoffflusses in Zentralstoffwechsel von Corynebacterium glutamicum mittels 13C-Isotopenanalyse," Forschungzentrum Jülich GmbH, 1997, with English language translation of the Table of Contents.

total ammonia concentration in medium (a)

pH of medium (b)

SEQUENCE LISTING

<160> NUMBER OF SEQ ID NOS: 18

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Primer ASK-F

<400> SEQUENCE: 1
cgcggatcct cgcgaagtag cacct gtcac tt                                32

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Primer ASK-R

<400> SEQUENCE: 2
ctcgggtacc gtgccacgga attcaatctt acggcc                            36

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Primer LysE-F

<400> SEQUENCE: 3
tggttaacgg gatttcagca agg                                          23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer LysE-R

<400> SEQUENCE: 4
gagcagctgg acaacagcct tga                                          23

<210> SEQ ID NO 5
<211> LENGTH: 1643
<212> TYPE: DNA
<213> ORGANISM: Brevibacterium lactofermentum
<220> FEATURE:
<221> NAME/KEY: CDS
<222> LOCATION: (217)..(1485)

<400> SEQUENCE: 5
tcgcgaagta gcacctgtca cttttgtctc aaatattaaa tcgaatatca atatacggtc    60
tgtttattgg aacgcatccc agtggctgag acgcatccgc taaagcccca ggaaccctgt   120
gcagaaagaa aacactcctc tggctaggta gacacagttt ataaaggtag agttgagcgg   180

-continued

| | | |
|---|---|---|
| gtaactgtca gcacgtagat cgaaaggtgc acaaag gtg gcc ctg gtc gta cag<br>                                                                               Val Ala Leu Val Val Gln<br>                                                                               1                   5 | 234 |
| aaa tat ggc ggt tcc tcg ctt gag agt gcg gaa cgc att aga aac gtc<br>Lys Tyr Gly Gly Ser Ser Leu Glu Ser Ala Glu Arg Ile Arg Asn Val<br>              10                   15                  20 | 282 |
| gct gaa cgg atc gtt gcc acc aag aag gct gga aat gat gtc gtg gtt<br>Ala Glu Arg Ile Val Ala Thr Lys Lys Ala Gly Asn Asp Val Val Val<br>        25                   30                   35 | 330 |
| gtc tgc tcc gca atg gga gac acc acg gat gaa ctt cta gaa ctt gca<br>Val Cys Ser Ala Met Gly Asp Thr Thr Asp Glu Leu Leu Glu Leu Ala<br>       40                  45                   50 | 378 |
| gcg gca gtg aat ccc gtt ccg cca gct cgt gaa atg gat atg ctc ctg<br>Ala Ala Val Asn Pro Val Pro Pro Ala Arg Glu Met Asp Met Leu Leu<br>55                  60                   65                      70 | 426 |
| act gct ggt gag cgt att tct aac gct ctc gtc gcc atg gct att gag<br>Thr Ala Gly Glu Arg Ile Ser Asn Ala Leu Val Ala Met Ala Ile Glu<br>               75                   80                 85 | 474 |
| tcc ctt ggc gca gaa gct caa tct ttc act ggc tct cag gct ggt gtg<br>Ser Leu Gly Ala Glu Ala Gln Ser Phe Thr Gly Ser Gln Ala Gly Val<br>          90                   95                 100 | 522 |
| ctc acc acc gag cgc cac gga aac gca cgc att gtt gac gtc aca ccg<br>Leu Thr Thr Glu Arg His Gly Asn Ala Arg Ile Val Asp Val Thr Pro<br>        105                 110                 115 | 570 |
| ggt cgt gtg cgt gaa gca ctc gat gag ggc aag atc tgc att gtt gct<br>Gly Arg Val Arg Glu Ala Leu Asp Glu Gly Lys Ile Cys Ile Val Ala<br>       120                 125                 130 | 618 |
| ggt ttt cag ggt gtt aat aaa gaa acc cgc gat gtc acc acg ttg ggt<br>Gly Phe Gln Gly Val Asn Lys Glu Thr Arg Asp Val Thr Thr Leu Gly<br>135                 140                 145                 150 | 666 |
| cgt ggt ggt tct gac acc act gca gtt gcg ttg gca gct gct ttg aac<br>Arg Gly Gly Ser Asp Thr Thr Ala Val Ala Leu Ala Ala Ala Leu Asn<br>                    155                 160                 165 | 714 |
| gct gat gtg tgt gag att tac tcg gac gtt gac ggt gtg tat acc gct<br>Ala Asp Val Cys Glu Ile Tyr Ser Asp Val Asp Gly Val Tyr Thr Ala<br>       170                 175                 180 | 762 |
| gac ccg cgc atc gtt cct aat gca cag aag ctg gaa aag ctc agc ttc<br>Asp Pro Arg Ile Val Pro Asn Ala Gln Lys Leu Glu Lys Leu Ser Phe<br>             185                 190                 195 | 810 |
| gaa gaa atg ctg gaa ctt gct gct gtt ggc tcc aag att ttg gtg ctg<br>Glu Glu Met Leu Glu Leu Ala Ala Val Gly Ser Lys Ile Leu Val Leu<br>200                 205                 210 | 858 |
| cgc agt gtt gaa tac gct cgt gca ttc aat gtg cca ctt cgc gta cgc<br>Arg Ser Val Glu Tyr Ala Arg Ala Phe Asn Val Pro Leu Arg Val Arg<br>215                 220                 225                 230 | 906 |
| tcg tct tat agt aat gat ccc ggc act ttg att gcc ggc tct atg gag<br>Ser Ser Tyr Ser Asn Asp Pro Gly Thr Leu Ile Ala Gly Ser Met Glu<br>                    235                 240                 245 | 954 |
| gat att cct gtg gaa gaa gca gtc ctt acc ggt gtc gca acc gac aag<br>Asp Ile Pro Val Glu Glu Ala Val Leu Thr Gly Val Ala Thr Asp Lys<br>       250                 255                 260 | 1002 |
| tcc gaa gcc aaa gta acc gtt ctg ggt att tcc gat aag cca ggc gag<br>Ser Glu Ala Lys Val Thr Val Leu Gly Ile Ser Asp Lys Pro Gly Glu<br>             265                 270                 275 | 1050 |
| act gcc aag gtt ttc cgt gcg ttg gct gat gca gaa atc aac att gac<br>Thr Ala Lys Val Phe Arg Ala Leu Ala Asp Ala Glu Ile Asn Ile Asp<br>       280                 285                 290 | 1098 |
| atg gtt ctg cag aac gtc tcc tct gtg gaa gac ggc acc acc gac atc<br>Met Val Leu Gln Asn Val Ser Ser Val Glu Asp Gly Thr Thr Asp Ile<br>295                 300                 305                 310 | 1146 |

```
acg ttc acc tgc cct cgc gct gac gga cgc cgt gcg atg gag atc ttg    1194
Thr Phe Thr Cys Pro Arg Ala Asp Gly Arg Arg Ala Met Glu Ile Leu
            315                 320                 325 aag aag ctt cag gtt cag ggc aac tgg acc aat gtg ctt tac gac gac    1242
Lys Lys Leu Gln Val Gln Gly Asn Trp Thr Asn Val Leu Tyr Asp Asp
        330                 335                 340 cag gtc ggc aaa gtc tcc ctc gtg ggt gct ggc atg aag tct cac cca    1290
Gln Val Gly Lys Val Ser Leu Val Gly Ala Gly Met Lys Ser His Pro
            345                 350                 355 ggt gtt acc gca gag ttc atg gaa gct ctg cgc gat gtc aac gtg aac    1338
Gly Val Thr Ala Glu Phe Met Glu Ala Leu Arg Asp Val Asn Val Asn
        360                 365                 370 atc gaa ttg att tcc acc tct gag atc cgc att tcc gtg ctg atc cgt    1386
Ile Glu Leu Ile Ser Thr Ser Glu Ile Arg Ile Ser Val Leu Ile Arg
375                 380                 385                 390 gaa gat gat ctg gat gct gct gca cgt gca ttg cat gag cag ttc cag    1434
Glu Asp Asp Leu Asp Ala Ala Ala Arg Ala Leu His Glu Gln Phe Gln
                395                 400                 405 ctg ggc ggc gaa gac gaa gcc gtc gtt tat gca ggc acc gga cgc taa    1482
Leu Gly Gly Glu Asp Glu Ala Val Val Tyr Ala Gly Thr Gly Arg
            410                 415                 420 agt tttaaggag tagttttaca atgaccacca tcgcagttgt tggtgcaacc          1535
Ser ggccaggtcg ccaggttat gcgcacccctt ttggaagagc gcaatttccc agctgacact  1595
gttcgtttct tgcttccccc gcgttccgca ggccgtaaga ttgaattc               1643

<210> SEQ ID NO 6
<211> LENGTH: 421
<212> TYPE: PRT
<213> ORGANISM: Brevibacterium lactofermentum

<400> SEQUENCE: 6

Val Ala Leu Val Val Gln Lys Tyr Gly Gly Ser Ser Leu Glu Ser Ala
 1               5                  10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190
```

```
Leu Glu Lys Leu Ser Phe Glu Glu Met Leu Glu Leu Ala Ala Val Gly
            195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
                260                 265                 270

Ser Asp Lys Pro Gly Glu Thr Ala Lys Val Phe Arg Ala Leu Ala Asp
            275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
            370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 7
<211> LENGTH: 1643
<212> TYPE: DNA
<213> ORGANISM: Brevibacterium lactofermentum
<220> FEATURE:
<221> NAME/KEY: CDS
<222> LOCATION: (964)..(1485)

<400> SEQUENCE: 7
tcgcgaagta gcacctgtca cttttgtctc aaatattaaa tcgaatatca atatacggtc      60
tgtttattgg aacgcatccc agtggctgag acgcatccgc taaagcccca ggaaccctgt     120
gcagaaagaa aacactcctc tggctaggta gacacagttt ataaaggtag agttgagcgg     180
gtaactgtca gcacgtagat cgaaaggtgc acaaggtggc cctggtcgt acagaaatat      240 ggcggttcct cgcttgagag tgcggaacgc attagaaacg tcgctgaacg gatcgttgcc     300
accaagaagg ctggaaatga tgtcgtggtt gtctgctccg caatgggaga caccacggat     360
gaacttctag aacttgcagc ggcagtgaat cccgttccgc agctcgtga aatggatatg      420 ctcctgactg ctggtgagcg tatttctaac gctctcgtcg ccatggctat tgagtccctt     480
ggcgcagaag ctcaatcttt cactggctct caggctggtg tgctcaccac cgagcgccac     540
ggaaacgcac gcattgttga cgtcacaccg gtcgtgtgc gtgaagcact cgatgagggc      600
aagatctgca ttgttgctgg ttttcagggt gttaataaag aaacccgcga tgtcaccacg     660
```

```
ttgggtcgtg gtggttctga caccactgca gttgcgttgg cagctgcttt gaacgctgat      720
gtgtgtgaga tttactcgga cgttgacggt gtgtataccg ctgacccgcg catcgttcct      780
aatgcacaga agctggaaaa gctcagcttc gaagaaatgc tggaacttgc tgctgttggc      840
tccaagattt tggtgctgcg cagtgttgaa tacgctcgtg cattcaatgt gccacttcgc      900
gtacgctcgt cttatagtaa tgatcccggc actttgattg ccggctctat ggaggatatt      960 cct gtg gaa gaa gca gtc ctt acc ggt gtc gca acc gac aag tcc gaa     1008
    Val Glu Glu Ala Val Leu Thr Gly Val Ala Thr Asp Lys Ser Glu
    1               5                   10                  15 gcc aaa gta acc gtt ctg ggt att tcc gat aag cca ggc gag act gcc     1056
Ala Lys Val Thr Val Leu Gly Ile Ser Asp Lys Pro Gly Glu Thr Ala
                20                  25                  30 aag gtt ttc cgt gcg ttg gct gat gca gaa atc aac att gac atg gtt     1104
Lys Val Phe Arg Ala Leu Ala Asp Ala Glu Ile Asn Ile Asp Met Val
            35                  40                  45 ctg cag aac gtc tcc tct gtg gaa gac ggc acc acc gac atc acg ttc     1152
Leu Gln Asn Val Ser Ser Val Glu Asp Gly Thr Thr Asp Ile Thr Phe
        50                  55                  60 acc tgc cct cgc gct gac gga cgc cgt gcg atg gag atc ttg aag aag     1200
Thr Cys Pro Arg Ala Asp Gly Arg Arg Ala Met Glu Ile Leu Lys Lys
65                  70                  75 ctt cag gtt cag ggc aac tgg acc aat gtg ctt tac gac gac cag gtc     1248
Leu Gln Val Gln Gly Asn Trp Thr Asn Val Leu Tyr Asp Asp Gln Val
    80                  85                  90                  95 ggc aaa gtc tcc ctc gtg ggt gct ggc atg aag tct cac cca ggt gtt     1296
Gly Lys Val Ser Leu Val Gly Ala Gly Met Lys Ser His Pro Gly Val
                100                 105                 110 acc gca gag ttc atg gaa gct ctg cgc gat gtc aac gtg aac atc gaa     1344
Thr Ala Glu Phe Met Glu Ala Leu Arg Asp Val Asn Val Asn Ile Glu
            115                 120                 125 ttg att tcc acc tct gag atc cgc att tcc gtg ctg atc cgt gaa gat     1392
Leu Ile Ser Thr Ser Glu Ile Arg Ile Ser Val Leu Ile Arg Glu Asp
        130                 135                 140 gat ctg gat gct gct gca cgt gca ttg cat gag cag ttc cag ctg ggc     1440
Asp Leu Asp Ala Ala Ala Arg Ala Leu His Glu Gln Phe Gln Leu Gly
145                 150                 155 ggc gaa gac gaa gcc gtc gtt tat gca ggc acc gga cgc taa agt         1485
Gly Glu Asp Glu Ala Val Val Tyr Ala Gly Thr Gly Arg         Ser
160                 165                 170 tttaaaggag tagttttaca atgaccacca tcgcagttgt tggtgcaacc ggccaggtcg     1545
gccaggttat gcgcaccctt ttggaagagc gcaatttccc agctgacact gttcgtttct     1605
ttgcttcccc gcgttccgca ggccgtaaga ttgaattc                              1643

<210> SEQ ID NO 8
<211> LENGTH: 172
<212> TYPE: PRT
<213> ORGANISM: Brevibacterium lactofermentum

<400> SEQUENCE: 8

Val Glu Glu Ala Val Leu Thr Gly Val Ala Thr Asp Lys Ser Glu Ala
1               5                   10                  15

Lys Val Thr Val Leu Gly Ile Ser Asp Lys Pro Gly Glu Thr Ala Lys
            20                  25                  30

Val Phe Arg Ala Leu Ala Asp Ala Glu Ile Asn Ile Asp Met Val Leu
        35                  40                  45

Gln Asn Val Ser Ser Val Glu Asp Gly Thr Thr Asp Ile Thr Phe Thr
    50                  55                  60
```

```
Cys Pro Arg Ala Asp Gly Arg Arg Ala Met Glu Ile Leu Lys Lys Leu
 65                  70                  75                  80

Gln Val Gln Gly Asn Trp Thr Asn Val Leu Tyr Asp Asp Gln Val Gly
             85                   90                  95

Lys Val Ser Leu Val Gly Ala Gly Met Lys Ser His Pro Gly Val Thr
        100                 105                 110

Ala Glu Phe Met Glu Ala Leu Arg Asp Val Asn Val Asn Ile Glu Leu
        115                 120                 125

Ile Ser Thr Ser Glu Ile Arg Ile Ser Val Leu Ile Arg Glu Asp Asp
130                 135                 140

Leu Asp Ala Ala Ala Arg Ala Leu His Glu Gln Phe Gln Leu Gly Gly
145                 150                 155                 160

Glu Asp Glu Ala Val Val Tyr Ala Gly Thr Gly Arg
             165                 170

<210> SEQ ID NO 9
<211> LENGTH: 2374
<212> TYPE: DNA
<213> ORGANISM: Corynebacterium glutamicum
<220> FEATURE:
<221> NAME/KEY: CDS
<222> LOCATION: (1025)..(1723)

<400> SEQUENCE: 9
ccatttgctg aaggtgttac tctgcctggc ccaattcctg cgggcgaaga agtgaaaaac        60
cctgaacctt ttcagaagta actaaggccg caatccctcg attgctgcat caacgacggc       120
gtctgtgagt ctagctagag atctagattc caggcgccat cgttgccaat acatcggtgt       180
gtcaatgggt atctcatcga ggaggatcac ttctcctgct tttagcatgg gagcagcttg       240
ggtttcggga agaagtcccc aaccaaggcc tcggcgaatt gcctcaccaa aaccttccgc       300
cgacgggaca atggatacgc gcctgcgccc cacaggacca tcgacgcgcc cgtccaggtc       360
acggtcttga agcacatctt tgggaccgaa gcgtaagacg ggcatcgcag cccaatctag       420
tttcccatca accatgtagg catcccgcaa tgagggggtt gcaatggcca agtggcgcat       480
ggttccaagt tctactactt cacatcccgc acgggattag cttcacggg ttaccgctcc        540 taaaacatct ccacgccgca gcaaggataa tgtgtgcgct tcatcttcca agcgcagcgt       600
gagcgttgct ccaccccaag aagctacctc gttgaacacg ggaggaaacc atgtggatag       660
cgaatctgcg ttgatggcga tggttaacgg gatttcagca aggcgtccag atagttgcgc       720
tttagtttct gcttgcagca acaccatttt ccgcgctgct tgcacaagga cttcacccgc       780
ttcggttgct ttggccggtt gggtgcgcga taccaacact cgacccacgt gatgctcgag       840
agctttaacg cgctgactca ccgccgaggg ggaaatggaa agggctaagg aggcgccttc       900
gaagctgcct tcatcaatga ttgagagcaa agtgtccagt tgaatggggt tcatgaagct       960
atattaaacc atgttaagaa ccaatcattt tacttaagta cttccatagg tcacgatggt      1020 gatc atg gaa atc ttc att aca ggt ctg ctt ttg ggg gcc agt ctt tta      1069
     Met Glu Ile Phe Ile Thr Gly Leu Leu Leu Gly Ala Ser Leu Leu
       1               5                  10                  15 ctg tcc atc gga ccg cag aat gta ctg gtg att aaa caa gga att aag      1117
Leu Ser Ile Gly Pro Gln Asn Val Leu Val Ile Lys Gln Gly Ile Lys
         20                  25                  30 cgc gaa gga ctc att gcg gtt ctt ctc gtg tgt tta att tct gac gtc      1165
Arg Glu Gly Leu Ile Ala Val Leu Leu Val Cys Leu Ile Ser Asp Val
     35                  40                  45
```

```
ttt ttg ttc atc gcc ggc acc ttg ggc gtt gat ctt ttg tcc aat gcc        1213
Phe Leu Phe Ile Ala Gly Thr Leu Gly Val Asp Leu Leu Ser Asn Ala
         50                  55                  60 gcg ccg atc gtg ctc gat att atg cgc tgg ggt ggc atc gct tac ctg        1261
Ala Pro Ile Val Leu Asp Ile Met Arg Trp Gly Gly Ile Ala Tyr Leu
 65                  70                  75 tta tgg ttt gcc gtc atg gca gcg aaa gac gcc atg aca aac aag gtg        1309
Leu Trp Phe Ala Val Met Ala Ala Lys Asp Ala Met Thr Asn Lys Val
 80                  85                  90                  95 gaa gcg cca cag atc att gaa gaa aca gaa cca acc gtg ccc gat gac        1357
Glu Ala Pro Gln Ile Ile Glu Glu Thr Glu Pro Thr Val Pro Asp Asp
             100                 105                 110 acg cct ttg ggc ggt tcg gcg gtg gcc act gac acg cgc aac cgg gtg        1405
Thr Pro Leu Gly Gly Ser Ala Val Ala Thr Asp Thr Arg Asn Arg Val
            115                 120                 125 cgg gtg gag gtg agc gtc gat aag cag cgg gtt tgg gta aag ccc atg        1453
Arg Val Glu Val Ser Val Asp Lys Gln Arg Val Trp Val Lys Pro Met
        130                 135                 140 ttg atg gca atc gtg ctg acc tgg ttg aac ccg aat gcg tat ttg gac        1501
Leu Met Ala Ile Val Leu Thr Trp Leu Asn Pro Asn Ala Tyr Leu Asp
145                 150                 155 gcg ttt gtg ttt atc ggc ggc gtc ggc gcg caa tac ggc gac acc gga        1549
Ala Phe Val Phe Ile Gly Gly Val Gly Ala Gln Tyr Gly Asp Thr Gly
160                 165                 170                 175 cgg tgg att ttc gcc gct ggc gcg ttc gcg gca agc ctg atc tgg ttc        1597
Arg Trp Ile Phe Ala Ala Gly Ala Phe Ala Ala Ser Leu Ile Trp Phe
                180                 185                 190 ccg ctg gtg ggt ttc ggc gca gca gca ttg tca cgc ccg ctg tcc agc        1645
Pro Leu Val Gly Phe Gly Ala Ala Ala Leu Ser Arg Pro Leu Ser Ser
            195                 200                 205 ccc aag gtg tgg cgc tgg atc aac gtc gtc gtg gca gtt gtg atg acc        1693
Pro Lys Val Trp Arg Trp Ile Asn Val Val Val Ala Val Val Met Thr
        210                 215                 220 gca ttg gcc atc aaa ctg atg ttg atg ggt tagttttcgc gggttttgga         1743
Ala Leu Ala Ile Lys Leu Met Leu Met Gly
225                 230 atcggtggcc ttcgcccaaa tgttgatgcc ggcgtcgtgg gaaatctcat cgatcgcctc      1803
caactcggcg tcagaaaact ccaagttgtt gagtgaatca aggctgttgt ccagctgctc      1863
aactgacgaa gcaccaatca atgcactggt cacggtatcc gcgccgtact ctccttgctc      1923
gcgcagcacc catgcaagcg ccatctgcgc aagtgactgc ccgcgttcct gggcgatgtc      1983
attgagcttg cggaccatat caatattgtt cacgttcaac atgccctcag acagggactt      2043
accctggctg gcgcgggaac cctctggaat tccatcgaga tatttgtccg tgagcaggcc      2103
ctgcgcaagt ggtgagaaag caatgacgcc aagaccattg ttggcagctg actgcaacaa      2163
gttctcaccg tcatcgcccg gttcctccac ccaacgatta atgatggaat agcttggctg      2223
atgaatcaga agcgggcagc cctcctccgc catgaactca gccgcctccg ctgtgagctc      2283
tggaccgtag aagaaatac  ccacgtaaag agcctttcca gacgcaacaa tgtcacgcaa      2343
tgcgtacatg gtttcttcca aaggagtatc t                                     2374

<210> SEQ ID NO 10
<211> LENGTH: 233
<212> TYPE: PRT
<213> ORGANISM: Corynebacterium glutamicum

<400> SEQUENCE: 10

Met Glu Ile Phe Ile Thr Gly Leu Leu Leu Gly Ala Ser Leu Leu Leu
```

```
              1               5                  10                 15
Ser Ile Gly Pro Gln Asn Val Leu Val Ile Lys Gln Gly Ile Lys Arg
                 20                    25                 30

Glu Gly Leu Ile Ala Val Leu Leu Val Cys Leu Ile Ser Asp Val Phe
         35                    40                 45

Leu Phe Ile Ala Gly Thr Leu Gly Val Asp Leu Leu Ser Asn Ala Ala
    50                    55                 60

Pro Ile Val Leu Asp Ile Met Arg Trp Gly Ile Ala Tyr Leu Leu
65                 70                 75                     80

Trp Phe Ala Val Met Ala Ala Lys Asp Ala Met Thr Asn Lys Val Glu
                     85                 90                 95

Ala Pro Gln Ile Ile Glu Glu Thr Glu Pro Thr Val Pro Asp Asp Thr
             100                   105                110

Pro Leu Gly Gly Ser Ala Val Ala Thr Asp Thr Arg Asn Arg Val Arg
             115                   120                125

Val Glu Val Ser Val Asp Lys Gln Arg Val Trp Val Lys Pro Met Leu
    130                   135                140

Met Ala Ile Val Leu Thr Trp Leu Asn Pro Asn Ala Tyr Leu Asp Ala
145                   150                155                160

Phe Val Phe Ile Gly Val Gly Ala Gln Tyr Gly Asp Thr Gly Arg
                 165                   170                175

Trp Ile Phe Ala Ala Gly Ala Phe Ala Ala Ser Leu Ile Trp Phe Pro
             180                   185                190

Leu Val Gly Phe Gly Ala Ala Ala Leu Ser Arg Pro Leu Ser Ser Pro
         195                   200                205

Lys Val Trp Arg Trp Ile Asn Val Val Val Ala Val Val Met Thr Ala
         210                   215                220

Leu Ala Ile Lys Leu Met Leu Met Gly
225                   230

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: cadA-attL

<400> SEQUENCE: 11
tttgctttct tctttcaata ccttaacggt atagcgtgaa gcctgctttt ttat          54

<210> SEQ ID NO 12
<211> LENGTH: 54
<212> TYPE: DNA
<213> ORGANISM: Artificial Sequence
<220> FEATURE:
<223> OTHER INFORMATION: Description of Artificial Sequence: cadA-attR

<400> SEQUENCE: 12
agatatgact atgaacgtta ttgcaatatt gaatcacgct caagttagta taaa          54

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: ldc-attL

<400> SEQUENCE: 13
ggaggaacac atgaacatca ttgccattat gggacctgaa gcctgctttt ttat          54
```

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence: ldcC-attR

<400> SEQUENCE: 14
cgccattttt aggactcgta cgcggtaaac gccgtccgtc aagttagtat aaa        53

<210> SEQ ID NO 15
<211> LENGTH: 2148
<212> TYPE: DNA
<213> ORGANISM: Escherichia coli
<220> FEATURE:
<221> NAME/KEY: CDS
<222> LOCATION: (1)..(2148)

<400> SEQUENCE: 15

| atg | aac | gtt | att | gca | ata | ttg | aat | cac | atg | ggg | gtt | tat | ttt | aaa | gaa | 48 |
| Met | Asn | Val | Ile | Ala | Ile | Leu | Asn | His | Met | Gly | Val | Tyr | Phe | Lys | Glu | |
| 1 | | | | 5 | | | | | 10 | | | | | 15 | | |

| gaa | ccc | atc | cgt | gaa | ctt | cat | cgc | gcg | ctt | gaa | cgt | ctg | aac | ttc | cag | 96 |
| Glu | Pro | Ile | Arg | Glu | Leu | His | Arg | Ala | Leu | Glu | Arg | Leu | Asn | Phe | Gln | |
| | | | 20 | | | | | 25 | | | | | 30 | | | |

| att | gtt | tac | ccg | aac | gac | cgt | gac | gac | tta | tta | aaa | ctg | atc | gaa | aac | 144 |
| Ile | Val | Tyr | Pro | Asn | Asp | Arg | Asp | Asp | Leu | Leu | Lys | Leu | Ile | Glu | Asn | |
| | | 35 | | | | | 40 | | | | | 45 | | | | |

| aat | gcg | cgt | ctg | tgc | ggc | gtt | att | ttt | gac | tgg | gat | aaa | tat | aat | ctc | 192 |
| Asn | Ala | Arg | Leu | Cys | Gly | Val | Ile | Phe | Asp | Trp | Asp | Lys | Tyr | Asn | Leu | |
| 50 | | | | | 55 | | | | | 60 | | | | | | |

| gag | ctg | tgc | gaa | gaa | att | agc | aaa | atg | aac | gag | aac | ctg | ccg | ttg | tac | 240 |
| Glu | Leu | Cys | Glu | Glu | Ile | Ser | Lys | Met | Asn | Glu | Asn | Leu | Pro | Leu | Tyr | |
| 65 | | | | | 70 | | | | | 75 | | | | | 80 | |

| gcg | ttc | gct | aat | acg | tat | tcc | act | ctc | gat | gta | agc | ctg | aat | gac | ctg | 288 |
| Ala | Phe | Ala | Asn | Thr | Tyr | Ser | Thr | Leu | Asp | Val | Ser | Leu | Asn | Asp | Leu | |
| | | | | 85 | | | | | 90 | | | | | 95 | | |

| cgt | tta | cag | att | agc | ttc | ttt | gaa | tat | gcg | ctg | ggt | gct | gct | gaa | gat | 336 |
| Arg | Leu | Gln | Ile | Ser | Phe | Phe | Glu | Tyr | Ala | Leu | Gly | Ala | Ala | Glu | Asp | |
| | | | 100 | | | | | 105 | | | | | 110 | | | |

| att | gct | aat | aag | atc | aag | cag | acc | act | gac | gaa | tat | atc | aac | act | att | 384 |
| Ile | Ala | Asn | Lys | Ile | Lys | Gln | Thr | Thr | Asp | Glu | Tyr | Ile | Asn | Thr | Ile | |
| | | 115 | | | | | 120 | | | | | 125 | | | | |

| ctg | cct | ccg | ctg | act | aaa | gca | ctg | ttt | aaa | tat | gtt | cgt | gaa | ggt | aaa | 432 |
| Leu | Pro | Pro | Leu | Thr | Lys | Ala | Leu | Phe | Lys | Tyr | Val | Arg | Glu | Gly | Lys | |
| | 130 | | | | | 135 | | | | | 140 | | | | | |

| tat | act | ttc | tgt | act | cct | ggt | cac | atg | ggc | ggt | act | gca | ttc | cag | aaa | 480 |
| Tyr | Thr | Phe | Cys | Thr | Pro | Gly | His | Met | Gly | Gly | Thr | Ala | Phe | Gln | Lys | |
| 145 | | | | | 150 | | | | | 155 | | | | | 160 | |

| agc | ccg | gta | ggt | agc | ctg | ttc | tat | gat | ttc | ttt | ggt | ccg | aat | acc | atg | 528 |
| Ser | Pro | Val | Gly | Ser | Leu | Phe | Tyr | Asp | Phe | Phe | Gly | Pro | Asn | Thr | Met | |
| | | | 165 | | | | | 170 | | | | | 175 | | | |

| aaa | tct | gat | att | tcc | att | tca | gta | tct | gaa | ctg | ggt | tct | ctg | ctg | gat | 576 |
| Lys | Ser | Asp | Ile | Ser | Ile | Ser | Val | Ser | Glu | Leu | Gly | Ser | Leu | Leu | Asp | |
| | | | 180 | | | | | 185 | | | | | 190 | | | |

| cac | agt | ggt | cca | cac | aaa | gaa | gca | gaa | cag | tat | atc | gct | cgc | gtc | ttt | 624 |
| His | Ser | Gly | Pro | His | Lys | Glu | Ala | Glu | Gln | Tyr | Ile | Ala | Arg | Val | Phe | |
| | | 195 | | | | | 200 | | | | | 205 | | | | |

| aac | gca | gac | cgc | agc | tac | atg | gtg | acc | aac | ggt | act | tcc | act | gcg | aac | 672 |
| Asn | Ala | Asp | Arg | Ser | Tyr | Met | Val | Thr | Asn | Gly | Thr | Ser | Thr | Ala | Asn | |
| 210 | | | | | 215 | | | | | 220 | | | | | | |

```
aaa att gtt ggt atg tac tct gct cca gca ggc agc acc att ctg att      720
Lys Ile Val Gly Met Tyr Ser Ala Pro Ala Gly Ser Thr Ile Leu Ile
225                 230                 235                 240 gac cgt aac tgc cac aaa tcg ctg acc cac ctg atg atg atg agc gat      768
Asp Arg Asn Cys His Lys Ser Leu Thr His Leu Met Met Met Ser Asp
                245                 250                 255 gtt acg cca atc tat ttc cgc ccg acc cgt aac gct tac ggt att ctt      816
Val Thr Pro Ile Tyr Phe Arg Pro Thr Arg Asn Ala Tyr Gly Ile Leu
            260                 265                 270 ggt ggt atc cca cag agt gaa ttc cag cac gct acc att gct aag cgc      864
Gly Gly Ile Pro Gln Ser Glu Phe Gln His Ala Thr Ile Ala Lys Arg
        275                 280                 285 gtg aaa gaa aca cca aac gca acc tgg ccg gta cat gct gta att acc      912
Val Lys Glu Thr Pro Asn Ala Thr Trp Pro Val His Ala Val Ile Thr
    290                 295                 300 aac tct acc tat gat ggt ctg ctg tac aac acc gac ttc atc aag aaa      960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac     1008
Thr Leu Asp Val Lys Ser Ile His Phe Asp Ser Ala Trp Val Pro Tyr
                325                 330                 335 acc aac ttc tca ccg att tac gaa ggt aaa tgc ggt atg agc ggt ggc     1056
Thr Asn Phe Ser Pro Ile Tyr Glu Gly Lys Cys Gly Met Ser Gly Gly
            340                 345                 350 cgt gta gaa ggg aaa gtg att tac gaa acc cag tcc act cac aaa ctg     1104
Arg Val Glu Gly Lys Val Ile Tyr Glu Thr Gln Ser Thr His Lys Leu
        355                 360                 365 ctg gcg gcg ttc tct cag gct tcc atg atc cac gtt aaa ggt gac gta     1152
Leu Ala Ala Phe Ser Gln Ala Ser Met Ile His Val Lys Gly Asp Val
    370                 375                 380 aac gaa gaa acc ttt aac gaa gcc tac atg atg cac acc acc act tct     1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg     1248
Pro His Tyr Gly Ile Val Ala Ser Thr Glu Thr Ala Ala Ala Met Met
                405                 410                 415 aaa ggc aat gca ggt aag cgt ctg atc aac ggt tct att gaa cgt gcg     1296
Lys Gly Asn Ala Gly Lys Arg Leu Ile Asn Gly Ser Ile Glu Arg Ala
            420                 425                 430 atc aaa ttc cgt aaa gag atc aaa cgt ctg aga acg gaa tct gat ggc     1344
Ile Lys Phe Arg Lys Glu Ile Lys Arg Leu Arg Thr Glu Ser Asp Gly
        435                 440                 445 tgg ttc ttt gat gta tgg cag ccg gat cat atc gat acg act gaa tgc     1392
Trp Phe Phe Asp Val Trp Gln Pro Asp His Ile Asp Thr Thr Glu Cys
    450                 455                 460 tgg ccg ctg cgt tct gac agc acc tgg cac ggc ttc aaa aac atc gat     1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg     1488
Asn Glu His Met Tyr Leu Asp Pro Ile Lys Val Thr Leu Leu Thr Pro
                485                 490                 495 ggg atg gaa aaa gac ggc acc atg agc gac ttt ggt att ccg gcc agc     1536
Gly Met Glu Lys Asp Gly Thr Met Ser Asp Phe Gly Ile Pro Ala Ser
            500                 505                 510 atc gtg gcg aaa tac ctc gac gaa cat ggc atc gtt gtt gag aaa acc     1584
Ile Val Ala Lys Tyr Leu Asp Glu His Gly Ile Val Val Glu Lys Thr
        515                 520                 525 ggt ccg tat aac ctg ctg ttc ctg ttc agc atc ggt atc gat aag acc     1632
Gly Pro Tyr Asn Leu Leu Phe Leu Phe Ser Ile Gly Ile Asp Lys Thr
```

```
                530             535             540
aaa gca ctg agc ctg ctg cgt gct ctg act gac ttt aaa cgt gcg ttc      1680
Lys Ala Leu Ser Leu Leu Arg Ala Leu Thr Asp Phe Lys Arg Ala Phe
545                 550             555                 560 gac ctg aac ctg cgt gtg aaa aac atg ctg ccg tct ctg tat cgt gaa      1728
Asp Leu Asn Leu Arg Val Lys Asn Met Leu Pro Ser Leu Tyr Arg Glu
                565             570             575 gat cct gaa ttc tat gaa aac atg cgt att cag gaa ctg gct cag aat      1776
Asp Pro Glu Phe Tyr Glu Asn Met Arg Ile Gln Glu Leu Ala Gln Asn
            580             585             590 atc cac aaa ctg att gtt cac cac aat ctg ccg gat ctg atg tat cgc      1824
Ile His Lys Leu Ile Val His His Asn Leu Pro Asp Leu Met Tyr Arg
        595             600             605 gca ttt gaa gtg ctg ccg acg atg gta atg act ccg tat gct gca ttc      1872
Ala Phe Glu Val Leu Pro Thr Met Val Met Thr Pro Tyr Ala Ala Phe
    610             615             620 cag aaa gag ctg cac ggt atg acc gaa gaa gtt tac ctc gac gaa atg      1920
Gln Lys Glu Leu His Gly Met Thr Glu Glu Val Tyr Leu Asp Glu Met
625             630             635             640 gta ggt cgt att aac gcc aat atg atc ctt ccg tac ccg ccg gga gtt      1968
Val Gly Arg Ile Asn Ala Asn Met Ile Leu Pro Tyr Pro Pro Gly Val
                645             650             655 cct ctg gta atg ccg ggt gaa atg atc acc gaa gaa agc cgt ccg gtt      2016
Pro Leu Val Met Pro Gly Glu Met Ile Thr Glu Glu Ser Arg Pro Val
            660             665             670 ctg gag ttc ctg cag atg ctg tgt gaa atc ggc gct cac tat ccg ggc      2064
Leu Glu Phe Leu Gln Met Leu Cys Glu Ile Gly Ala His Tyr Pro Gly
        675             680             685 ttt gaa acc gat att cac ggt gca tac cgt cag gct gat ggc cgc tat      2112
Phe Glu Thr Asp Ile His Gly Ala Tyr Arg Gln Ala Asp Gly Arg Tyr
    690             695             700 acc gtt aag gta ttg aaa gaa gaa agc aaa aaa taa                      2148
Thr Val Lys Val Leu Lys Glu Glu Ser Lys Lys
705             710             715

<210> SEQ ID NO 16
<211> LENGTH: 715
<212> TYPE: PRT
<213> ORGANISM: Escherichia coli

<400> SEQUENCE: 16

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
```

-continued

```
            130                 135                 140
Tyr Thr Phe Cys Thr Pro Gly His Met Gly Thr Ala Phe Gln Lys
145                 150                 155                 160

Ser Pro Val Gly Ser Leu Phe Tyr Asp Phe Gly Pro Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Gln Tyr Ile Ala Arg Val Phe
                195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
                275                 280                 285

Val Lys Glu Thr Pro Asn Ala Thr Trp Pro Val His Ala Val Ile Thr
                290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
                370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445

Trp Phe Phe Asp Val Trp Gln Pro Asp His Ile Asp Thr Thr Glu Cys
                450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
                530                 535                 540

Lys Ala Leu Ser Leu Leu Arg Ala Leu Thr Asp Phe Lys Arg Ala Phe
545                 550                 555                 560
```

```
Asp Leu Asn Leu Arg Val Lys Asn Met Leu Pro Ser Leu Tyr Arg Glu
            565                 570                 575

Asp Pro Glu Phe Tyr Glu Asn Met Arg Ile Gln Glu Leu Ala Gln Asn
        580                 585                 590

Ile His Lys Leu Ile Val His His Asn Leu Pro Asp Leu Met Tyr Arg
            595                 600                 605

Ala Phe Glu Val Leu Pro Thr Met Val Met Thr Pro Tyr Ala Ala Phe
        610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
            645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
        690                 695                 700

Thr Val Lys Val Leu Lys Glu Glu Ser Lys Lys
705                 710                 715

<210> SEQ ID NO 17
<211> LENGTH: 2142
<212> TYPE: DNA
<213> ORGANISM: Escherichia coli
<220> FEATURE:
<221> NAME/KEY: CDS
<222> LOCATION: (1)..(2142)

<400> SEQUENCE: 17 atg aac atc att gcc att atg gga ccg cat ggc gtc ttt tat aaa gat    48
Met Asn Ile Ile Ala Ile Met Gly Pro His Gly Val Phe Tyr Lys Asp
  1               5                  10                  15 gag ccc atc aaa gaa ctg gag tcg gcg ctg gtg gcg caa ggc ttt cag    96
Glu Pro Ile Lys Glu Leu Glu Ser Ala Leu Val Ala Gln Gly Phe Gln
             20                  25                  30 att atc tgg cca caa aac agc gtt gat ttg ctg aaa ttt atc gag cat   144
Ile Ile Trp Pro Gln Asn Ser Val Asp Leu Leu Lys Phe Ile Glu His
         35                  40                  45 aac cct cga att tgc ggc gtg att ttt gac tgg gat gag tac agt ctc   192
Asn Pro Arg Ile Cys Gly Val Ile Phe Asp Trp Asp Glu Tyr Ser Leu
     50                  55                  60 gat tta tgt agc gat atc aat cag ctt aat gaa tat ctc ccg ctt tat   240
Asp Leu Cys Ser Asp Ile Asn Gln Leu Asn Glu Tyr Leu Pro Leu Tyr
 65                  70                  75                  80 gcc ttc atc aac acc cac tcg acg atg gat gtc agc gtg cag gat atg   288
Ala Phe Ile Asn Thr His Ser Thr Met Asp Val Ser Val Gln Asp Met
                 85                  90                  95 cgg atg gcg ctc tgg ttt ttt gaa tat gcg ctg ggg cag gcg gaa gat   336
Arg Met Ala Leu Trp Phe Phe Glu Tyr Ala Leu Gly Gln Ala Glu Asp
            100                 105                 110 atc gcc att cgt atg cgt cag tac acc gac gaa tat ctt gat aac att   384
Ile Ala Ile Arg Met Arg Gln Tyr Thr Asp Glu Tyr Leu Asp Asn Ile
        115                 120                 125 aca ccg ccg ttc acg aaa gcc ttg ttt acc tac gtc aaa gag cgg aag   432
Thr Pro Pro Phe Thr Lys Ala Leu Phe Thr Tyr Val Lys Glu Arg Lys
    130                 135                 140 tac acc ttt tgt acg ccg ggg cat atg ggc ggc acc gca tat caa aaa   480
```

-continued

| | | |
|---|---|---|
| Tyr Thr Phe Cys Thr Pro Gly His Met Gly Thr Ala Tyr Gln Lys<br>145                  150                        155                      160 | |
| agc ccg gtt ggc tgt ctg ttt tat gat ttt ttc ggc ggg aat act ctt<br>Ser Pro Val Gly Cys Leu Phe Tyr Asp Phe Phe Gly Gly Asn Thr Leu<br>                      165                      170                        175 | 528 |
| aag gct gat gtc tct att tcg gtc acc gag ctt ggt tcg ttg ctc gac<br>Lys Ala Asp Val Ser Ile Ser Val Thr Glu Leu Gly Ser Leu Leu Asp<br>            180                      185                      190 | 576 |
| cac acc ggg cca cac ctg gaa gcg gaa gag tac atc gcg cgg act ttt<br>His Thr Gly Pro His Leu Glu Ala Glu Glu Tyr Ile Ala Arg Thr Phe<br>                195                      200                      205 | 624 |
| ggc gcg gaa cag agt tat atc gtt acc aac gga aca tcg acg tcg aac<br>Gly Ala Glu Gln Ser Tyr Ile Val Thr Asn Gly Thr Ser Thr Ser Asn<br>210                        215                      220 | 672 |
| aaa att gtg ggt atg tac gcc gcg cca tcc ggc agt acg ctg ttg atc<br>Lys Ile Val Gly Met Tyr Ala Ala Pro Ser Gly Ser Thr Leu Leu Ile<br>225                        230                      235                      240 | 720 |
| gac cgc aat tgt cat aaa tcg ctg gcg cat ctg ttg atg atg aac gat<br>Asp Arg Asn Cys His Lys Ser Leu Ala His Leu Leu Met Met Asn Asp<br>                      245                      250                      255 | 768 |
| gta gtg cca gtc tgg ctg aaa ccg acg cgt aat gcg ttg ggg att ctt<br>Val Val Pro Val Trp Leu Lys Pro Thr Arg Asn Ala Leu Gly Ile Leu<br>            260                      265                      270 | 816 |
| ggt ggg atc ccg cgc cgt gaa ttt act cgc gac agc atc gaa gag aaa<br>Gly Gly Ile Pro Arg Arg Glu Phe Thr Arg Asp Ser Ile Glu Glu Lys<br>                275                      280                      285 | 864 |
| gtc gct gct acc acg caa gca caa tgg ccg gtt cat gcg gtg atc acc<br>Val Ala Ala Thr Thr Gln Ala Gln Trp Pro Val His Ala Val Ile Thr<br>290                        295                      300 | 912 |
| aac tcc acc tat gat ggc ttg ctc tac aac acc gac tgg atc aaa cag<br>Asn Ser Thr Tyr Asp Gly Leu Leu Tyr Asn Thr Asp Trp Ile Lys Gln<br>305                        310                      315                      320 | 960 |
| acg ctg gat gtc ccg tcg att cac ttc gat tct gcc tgg gtg ccg tac<br>Thr Leu Asp Val Pro Ser Ile His Phe Asp Ser Ala Trp Val Pro Tyr<br>                325                      330                      335 | 1008 |
| acc cat ttt cat ccg atc tac cag ggt aaa agt ggt atg agc ggc gag<br>Thr His Phe His Pro Ile Tyr Gln Gly Lys Ser Gly Met Ser Gly Glu<br>                340                      345                      350 | 1056 |
| cgt gtt gcg gga aaa gtg atc ttc gaa acg caa tcg acc cac aaa atg<br>Arg Val Ala Gly Lys Val Ile Phe Glu Thr Gln Ser Thr His Lys Met<br>            355                      360                      365 | 1104 |
| ctg gcg gcg tta tcg cag gct tcg ctg atc cac att aaa ggc gag tat<br>Leu Ala Ala Leu Ser Gln Ala Ser Leu Ile His Ile Lys Gly Glu Tyr<br>370                        375                      380 | 1152 |
| gac gaa gag gcc ttt aac gaa gcc ttt atg atg cat acc acc acc tcg<br>Asp Glu Glu Ala Phe Asn Glu Ala Phe Met Met His Thr Thr Thr Ser<br>385                        390                      395                      400 | 1200 |
| ccc agt tat ccc att gtt gct tcg gtt gag acg gcg gcg gcg atg ctg<br>Pro Ser Tyr Pro Ile Val Ala Ser Val Glu Thr Ala Ala Ala Met Leu<br>                405                      410                      415 | 1248 |
| cgt ggt aat ccg ggc aaa cgg ctg att aac cgt tca gta gaa cga gct<br>Arg Gly Asn Pro Gly Lys Arg Leu Ile Asn Arg Ser Val Glu Arg Ala<br>            420                      425                      430 | 1296 |
| ctg cat ttt cgc aaa gag gtc cag cgg ctg cgg gaa gag tct gac ggt<br>Leu His Phe Arg Lys Glu Val Gln Arg Leu Arg Glu Glu Ser Asp Gly<br>                435                      440                      445 | 1344 |
| tgg ttt ttc gat atc tgg caa ccg ccg cag gtg gat gaa gcc gaa tgc<br>Trp Phe Phe Asp Ile Trp Gln Pro Pro Gln Val Asp Glu Ala Glu Cys<br>450                        455                      460 | 1392 |

| | | |
|---|---|---|
| tgg ccc gtt gcg cct ggc gaa cag tgg cac ggc ttt aac gat gcg gat<br>Trp Pro Val Ala Pro Gly Glu Gln Trp His Gly Phe Asn Asp Ala Asp<br>465                     470                        475                    480 | 1440 |
| gcc gat cat atg ttt ctc gat ccg gtt aaa gtc act att ttg aca ccg<br>Ala Asp His Met Phe Leu Asp Pro Val Lys Val Thr Ile Leu Thr Pro<br>                     485                        490                    495 | 1488 |
| ggg atg gac gag cag ggc aat atg agc gag gag ggg atc ccg gcg gcg<br>Gly Met Asp Glu Gln Gly Asn Met Ser Glu Glu Gly Ile Pro Ala Ala<br>500                     505                        510 | 1536 |
| ctg gta gca aaa ttc ctc gac gaa cgt ggg atc gta gta gag aaa acc<br>Leu Val Ala Lys Phe Leu Asp Glu Arg Gly Ile Val Val Glu Lys Thr<br>                     515                        520                    525 | 1584 |
| ggc cct tat aac ctg ctg ttt ctc ttt agt att ggc atc gat aaa acc<br>Gly Pro Tyr Asn Leu Leu Phe Leu Phe Ser Ile Gly Ile Asp Lys Thr<br>530                     535                        540 | 1632 |
| aaa gca atg gga tta ttg cgt ggg ttg acg gaa ttc aaa cgc tct tac<br>Lys Ala Met Gly Leu Leu Arg Gly Leu Thr Glu Phe Lys Arg Ser Tyr<br>545                     550                        555                    560 | 1680 |
| gat ctc aac ctg cgg atc aaa aat atg cta ccc gat ctc tat gca gaa<br>Asp Leu Asn Leu Arg Ile Lys Asn Met Leu Pro Asp Leu Tyr Ala Glu<br>                     565                        570                    575 | 1728 |
| gat ccc gat ttc tac cgc aat atg cgt att cag gat ctg gca caa ggg<br>Asp Pro Asp Phe Tyr Arg Asn Met Arg Ile Gln Asp Leu Ala Gln Gly<br>580                     585                        590 | 1776 |
| atc cat aag ctg att cgt aaa cac gat ctt ccc ggt ttg atg ttg cgg<br>Ile His Lys Leu Ile Arg Lys His Asp Leu Pro Gly Leu Met Leu Arg<br>595                     600                        605 | 1824 |
| gca ttc gat act ttg ccg gag atg atc atg acg cca cat cag gca tgg<br>Ala Phe Asp Thr Leu Pro Glu Met Ile Met Thr Pro His Gln Ala Trp<br>610                     615                        620 | 1872 |
| caa cga caa att aaa ggc gaa gta gaa acc att gcg ctg gaa caa ctg<br>Gln Arg Gln Ile Lys Gly Glu Val Glu Thr Ile Ala Leu Glu Gln Leu<br>625                     630                        635                    640 | 1920 |
| gtc ggt aga gta tcg gca aat atg atc ctg cct tat cca ccg ggc gta<br>Val Gly Arg Val Ser Ala Asn Met Ile Leu Pro Tyr Pro Pro Gly Val<br>                     645                        650                    655 | 1968 |
| ccg ctg ttg atg cct gga gaa atg ctg acc aaa gag agc cgc aca gta<br>Pro Leu Leu Met Pro Gly Glu Met Leu Thr Lys Glu Ser Arg Thr Val<br>660                     665                        670 | 2016 |
| ctc gat ttt cta ctg atg ctt tgt tcc gtc ggg caa cat tac ccc ggt<br>Leu Asp Phe Leu Leu Met Leu Cys Ser Val Gly Gln His Tyr Pro Gly<br>                     675                        680                    685 | 2064 |
| ttt gaa acg gat att cac ggc gcg aaa cag gac gaa gac ggc gtt tac<br>Phe Glu Thr Asp Ile His Gly Ala Lys Gln Asp Glu Asp Gly Val Tyr<br>690                     695                        700 | 2112 |
| cgc gta cga gtc cta aaa atg gcg gga taa<br>Arg Val Arg Val Leu Lys Met Ala Gly<br>705                     710 | 2142 |

<210> SEQ ID NO 18
<211> LENGTH: 713
<212> TYPE: PRT
<213> ORGANISM: Escherichia coli

<400> SEQUENCE: 18

Met Asn Ile Ile Ala Ile Met Gly Pro His Gly Val Phe Tyr Lys Asp
1                 5                   10                 15

Glu Pro Ile Lys Glu Leu Glu Ser Ala Leu Val Ala Gln Gly Phe Gln
                   20                   25                 30

Ile Ile Trp Pro Gln Asn Ser Val Asp Leu Leu Lys Phe Ile Glu His

```
                35                  40                  45
Asn Pro Arg Ile Cys Gly Val Ile Phe Asp Trp Asp Glu Tyr Ser Leu
 50                  55                  60
Asp Leu Cys Ser Asp Ile Asn Gln Leu Asn Glu Tyr Leu Pro Leu Tyr
 65                  70                  75                  80
Ala Phe Ile Asn Thr His Ser Thr Met Asp Val Ser Val Gln Asp Met
                 85                  90                  95
Arg Met Ala Leu Trp Phe Phe Glu Tyr Ala Leu Gly Gln Ala Glu Asp
                100                 105                 110
Ile Ala Ile Arg Met Arg Gln Tyr Thr Asp Glu Tyr Leu Asp Asn Ile
            115                 120                 125
Thr Pro Pro Phe Thr Lys Ala Leu Phe Thr Tyr Val Lys Glu Arg Lys
130                 135                 140
Tyr Thr Phe Cys Thr Pro Gly His Met Gly Gly Thr Ala Tyr Gln Lys
145                 150                 155                 160
Ser Pro Val Gly Cys Leu Phe Tyr Asp Phe Phe Gly Asn Thr Leu
                165                 170                 175
Lys Ala Asp Val Ser Ile Ser Val Thr Glu Leu Gly Ser Leu Leu Asp
                180                 185                 190
His Thr Gly Pro His Leu Glu Ala Glu Tyr Ile Ala Arg Thr Phe
                195                 200                 205
Gly Ala Glu Gln Ser Tyr Ile Val Thr Asn Gly Thr Ser Thr Ser Asn
210                 215                 220
Lys Ile Val Gly Met Tyr Ala Ala Pro Ser Gly Ser Thr Leu Leu Ile
225                 230                 235                 240
Asp Arg Asn Cys His Lys Ser Leu Ala His Leu Leu Met Met Asn Asp
                245                 250                 255
Val Val Pro Val Trp Leu Lys Pro Thr Arg Asn Ala Leu Gly Ile Leu
                260                 265                 270
Gly Gly Ile Pro Arg Arg Glu Phe Thr Arg Asp Ser Ile Glu Glu Lys
            275                 280                 285
Val Ala Ala Thr Thr Gln Ala Gln Trp Pro Val His Ala Val Ile Thr
290                 295                 300
Asn Ser Thr Tyr Asp Gly Leu Leu Tyr Asn Thr Asp Trp Ile Lys Gln
305                 310                 315                 320
Thr Leu Asp Val Pro Ser Ile His Phe Asp Ser Ala Trp Val Pro Tyr
                325                 330                 335
Thr His Phe His Pro Ile Tyr Gln Gly Lys Ser Gly Met Ser Gly Glu
                340                 345                 350
Arg Val Ala Gly Lys Val Ile Phe Glu Thr Gln Ser Thr His Lys Met
            355                 360                 365
Leu Ala Ala Leu Ser Gln Ala Ser Leu Ile His Ile Lys Gly Glu Tyr
            370                 375                 380
Asp Glu Glu Ala Phe Asn Glu Ala Phe Met Met His Thr Thr Thr Ser
385                 390                 395                 400
Pro Ser Tyr Pro Ile Val Ala Ser Val Glu Thr Ala Ala Ala Met Leu
                405                 410                 415
Arg Gly Asn Pro Gly Lys Arg Leu Ile Asn Arg Ser Val Glu Arg Ala
                420                 425                 430
Leu His Phe Arg Lys Glu Val Gln Arg Leu Arg Glu Glu Ser Asp Gly
            435                 440                 445
Trp Phe Phe Asp Ile Trp Gln Pro Pro Gln Val Asp Glu Ala Glu Cys
450                 455                 460
```

-continued

```
Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
                485                 490                 495

Gly Met Asp Glu Gln Gly Asn Met Ser Glu Glu Gly Ile Pro Ala Ala
            500                 505                 510

Leu Val Ala Lys Phe Leu Asp Glu Arg Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
        595                 600                 605

Ala Phe Asp Thr Leu Pro Glu Met Ile Met Thr Pro His Gln Ala Trp
610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly
        675                 680                 685

Phe Glu Thr Asp Ile His Gly Ala Lys Gln Asp Glu Asp Gly Val Tyr
    690                 695                 700

Arg Val Arg Val Leu Lys Met Ala Gly
705                 710
```

METHOD FOR PRODUCING BASIC SUBSTANCE

This application is a divisional of, and claims priority under 35 U.S.C. §120 of U.S. patent application Ser. No. 12/834,381, filed Jul. 12, 2010 now U.S. Pat. No. 8,198,053, which was a divisional under 35 U.S.C. §120 of Ser. No. 11/697,794, filed Apr. 9, 2007 now U.S. Pat. No. 7,790,422, which was a continuation under 35 U.S.C. §120 of PCT/JP2005/018657, filed Oct. 7, 2005, and claimed priority under 35 U.S.C. §119 to JP2004-295123, filed Oct. 7, 2004, all of which are incorporated by reference. The Sequence Listing filed electronically herewith is also hereby incorporated by reference in its entirety (File Name: 2012-02-24T_US-328D2-Seq_List; File Size: 55 KB; Date Created Feb. 24, 2012).

BACKGROUND OF THE INVENTION

1. Field of the Invention

The present invention relates to a technique for the microbial industry, more precisely, a method for producing a basic substance by fermentation. As basic substances which are able to be produced by fermentation, for example, L-lysine is useful as an additive in animal feed, and L-arginine and L-histidine are useful for pharmaceutical preparations such as infusions.

2. Brief Description of the Related Art

In the methods for producing basic substances by fermentation, microorganisms having an ability to produce a basic substance are cultured to produce and accumulate the basic substance in a medium, and the basic substance is collected from the medium. In such methods, the culture is performed as batch culture, feeding culture or continuous culture.

In such production of basic substances by fermentation, sulfate or chloride ions have been typically added to a medium as counter anions for an objective substance which dissociates into a cation in the medium in order to maintain pH of the medium at a neutral level (Japanese Patent Laid-open (Kokai) Nos. 5-30985 and 5-244969).

In many cases, basic substances are collected from a medium by ion exchange, when purification is required. For example, in the case of L-lysine, after fermentation broth is made weakly acidic, L-lysine is adsorbed on an ion exchange resin and then eluted from the resin with ammonium ions. The eluted L-lysine is used as it is as lysine base, or it can be crystallized with hydrochloric acid to form L-lysine hydrochloride.

When chloride ions are used as counter anions in the medium in the aforementioned purification of L-lysine, L-lysine hydrochloride can be obtained directly by concentrating the medium. However, since chloride ions corrode metal fermentation tanks etc., it is not preferable to make them exist in the medium in high concentration in actual production.

On the other hand, when the basic substance is not purified, the fermentation broth is concentrated as it is, or it is made weakly acidic with hydrochloric acid or sulfuric acid, followed by spray granulation. In this case, the residual components contain the counter anions added to the medium, and therefore the amount of the basic substance is reduced in the resulting fermentation product.

Japanese Patent Laid-open No. 2002-65287 (U.S. Patent Application No. 2002025564) discloses a method of utilizing, in the production of a basic amino acid by fermentation, carbonate and bicarbonate ions as counter anions of the basic amino acid to substitute for a part of sulfate or chloride ions. Carbonate and bicarbonate ions can be comparatively easily removed from the culture medium by making the pH of the medium acidic, or concentrating the medium, or both. The above-cited publication teaches a method of controlling the internal pressure in the fermentation tank so that it is positive during fermentation, or adding carbon dioxide gas or a mixed gas containing carbon dioxide to the medium, as a means for adding carbonate ions and bicarbonate ions to the medium. However, at typical medium conditions, such as a neutral pH, only a small amount of carbon dioxide gas dissolves, if at all. Therefore, to maintain the presence of bicarbonate and carbonate ions in the culture medium so that the effect of reducing the sulfate or chloride ion concentration is maintained, the culture must be performed at an alkaline pH. However, if pH becomes high, the bacterial growth rate and productivity of the objective substance are generally reduced.

SUMMARY OF THE INVENTION

An object of the present invention is to provide a method for achieving both reduction of sulfate ions and chloride ions and efficient production of an objective substance in the production of a basic substance by fermentation using a microorganism having an ability to produce the objective basic substance and utilizing carbonate ions and bicarbonate ions as counter anions of the basic substance with avoiding reduction of growth rate of the microorganism or reduction of productivity of the objective substance.

When using coryneform or *Escherichia* bacteria to produce basic substances by fermentation, if pH becomes too high, the bacterial growth rate or the productivity of the objective substance is usually reduced. The inventors of the present invention found that the major factor causing this phenomenon is ammonia, which is added to the medium as a nitrogen source for production of the basic substance, for bacterial growth, or as a source of counter ions of the basic substance, and reduction of the growth rate of the microorganism or the productivity of the objective substance under a high pH condition could be markedly suppressed by performing the fermentation with controlling the total ammonia concentration to be within a suitable concentration range.

The present invention was accomplished on the basis of the aforementioned findings.

That is, the present invention provides the followings.

(1) A method for producing a basic substance by fermentation comprising culturing a microorganism having an ability to produce the basic substance in a liquid medium contained in a fermentation tank to produce and accumulate the basic substance in the medium, wherein amount of sulfate and/or chloride ions used as counter ions of the basic substance is reduced by adjusting total ammonia concentration in the medium to be within a specific concentration range during at least a part of the total period of culture process.

(2) The method according to (1), wherein the specific concentration range of the total ammonia concentration is a range satisfying the following conditions:

(A) concentration of ammonium ions in the medium is at such a level that the sum of the ion equivalents of bicarbonate ions and/or carbonate ions and other anions dissolved in the medium is larger than the ion equivalent of the basic substance ionized from the basic substance accumulated in the medium, and (B) the total ammonia concentration in the medium is at a level not inhibiting the production of the basic substance by the microorganism, which is determined beforehand as follows:

the microorganism is cultured in the medium having various pH values and various total ammonia concentrations, productivity of the basic substance is measured at each pH value and each total ammonia concentration, and a total ammonia concentration providing 50% or more of productivity of the basic substance based on the productivity obtained under optimum conditions is determined for each pH value.

(3) The method according to (1), wherein the specific range of the total ammonia concentration is determined beforehand as follows:

(A') the culture is performed in a medium which contains sulfate and/or chloride ions in an amount sufficient for performing the culture at pH 7.2 or lower as a source of counter ions of the objective basic substance, of which pH is maintained to be in the range between 6.5 to 7.2 by adding at least one of ammonia gas, aqueous ammonia and urea, and productivity of the basic substance is measured, (B') the culture is started in the same medium as that used in the step (A') except that sulfate ions and/or chloride ions of medium components are lowered by a desired amount, and the culture is continued with various total ammonia concentrations during a period where it becomes impossible to maintain the pH of the medium to be 7.2 or lower due to the shortage of sulfate ions and/or chloride ions as counter ions of the basic substance caused by accumulation of the objective basic substance to determine a total ammonia concentration range providing 50% or more of productivity based on the productivity measured in the step (A').

(4) The method according to (1), wherein the at least a part of the total period includes at least one of a period where the pH of the medium increases due to shortage of the counter ions caused with accumulation of the objective basic substance, and a period where the pH increases due to the addition of cations to the medium.

(5) The method according to (1), wherein the total ammonia concentration in the medium is adjusted by adding ammonia or urea to the medium when the activity of the microorganism is reduced or ceases as determined based on the indicators: dissolved oxygen concentration in the medium, consumption rate of carbon source in the medium, turbidity of the medium, productivity of the basic substance, and pH change in the medium observed.

(6) The method according to (1), wherein a medium having the same composition as that of a medium containing sulfate ions and/or chloride ions as a counter ion source of the basic substance in an amount sufficient for performing the culture at pH 7.2 or lower except that amount of sulfate ions and/or chloride ions is reduced by a desired amount is used as the medium, and the at least a part of the total period is a period where pH of the medium cannot be maintained to be 7.2 or lower due to shortage of counter ions for the basic substance which has accumulated in the medium.

(7) The method according to (2), wherein the other anions are selected from sulfate ions, chloride ions, phosphate ions, and ionized organic acids.

(8) The method according to (2) or (7), wherein total amount of the other anions is 900 meq/l or lower.

(9) The method according to (1), wherein the total ammonia concentration in the medium is adjusted to be 200 mM or lower.

(10) The method according to (1), which comprises the step of proliferating the microorganism.

(11) The method according to (10), wherein the total ammonia concentration is not adjusted during the step of proliferating the microorganism.

(12) The method according to (1), wherein the basic substance is selected from L-lysine, L-arginine and L-histidine.

(13) The method according to (12), wherein the basic substance is L-lysine.

(14) The method according to (12), wherein the basic substance is L-arginine.

(15) The method according to (1), wherein the medium or a processed product thereof is heated after the fermentation to eliminate bicarbonate ions and carbonate ions.

(16) The method according to (1), wherein the microorganism is a coryneform bacterium or an *Escherichia* bacterium.

(17) A fermentation broth or fermentation product containing a basic substance, which is obtainable by the method according to (15).

BRIEF DESCRIPTION OF THE DRAWINGS

FIG. 1a shows the growth curve over time at two different pH values. FIG. 1b shows the lysine accumulation over time at two different pH values. FIG. 1c shows the ammonia concentration over time at two different pH values.

FIG. 2a shows the growth curve over time at three different pH values. FIG. 2b shows the lysine accumulation over time at three different pH values. FIG. 2c shows the ammonia concentration over time at three different pH values.

FIG. 3a shows the growth curve over time. FIG. 3b shows the lysine accumulation over time. FIG. 3c shows the ammonia concentration over time.

DESCRIPTION OF THE PREFERRED EMBODIMENTS

Figure 1:
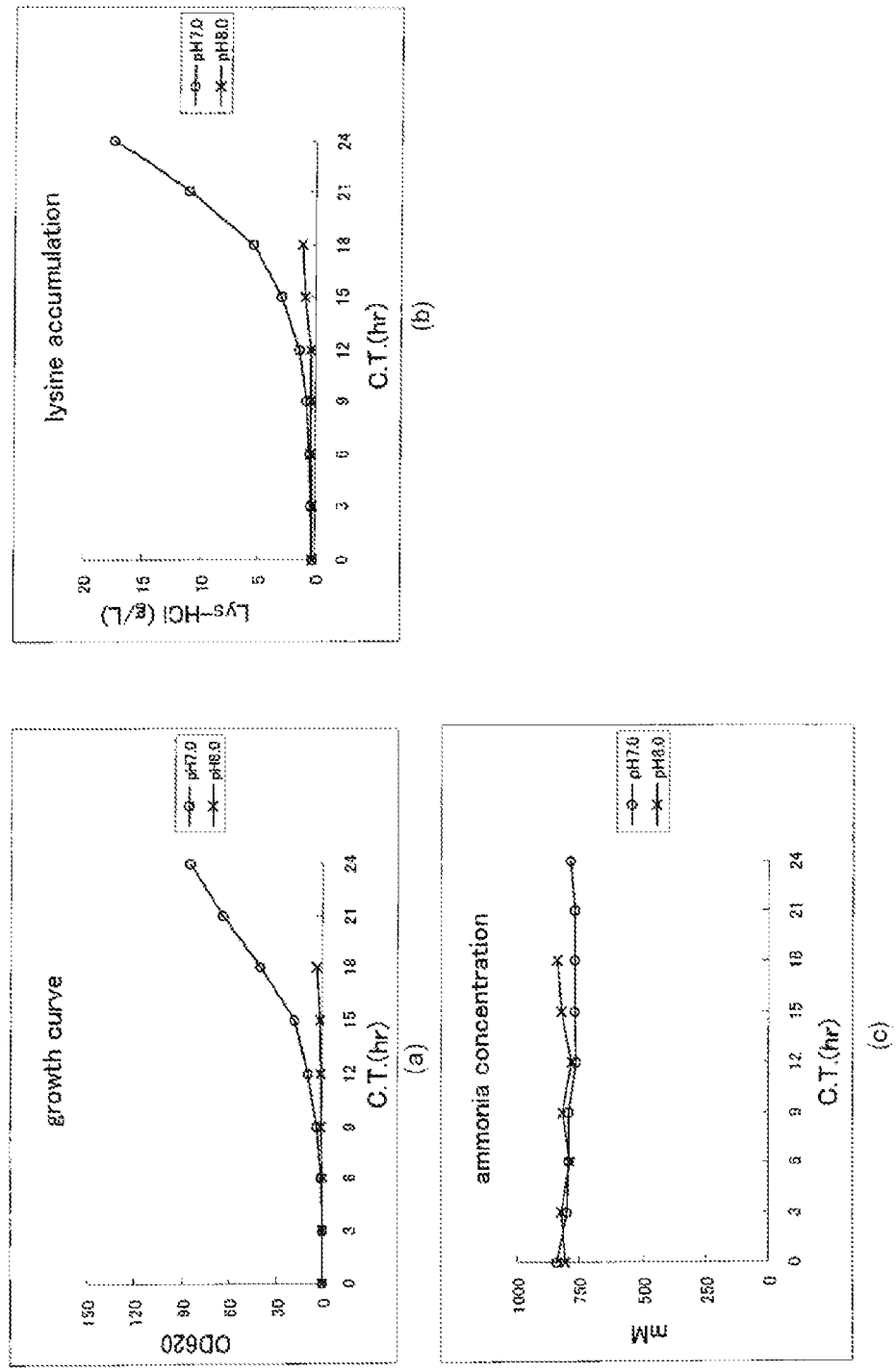
FIG. 1 shows the results of culture for L-lysine production performed by using a conventional medium and the culture method.

Hereafter, the present invention will be explained in detail.

The method of the present invention is a method for producing a basic substance by fermentation, which comprises culturing a microorganism which is able to produce the basic substance in a liquid medium contained in a fermentation tank to produce and accumulate the basic substance in the medium. The method of the present invention is characterized in that amount of sulfate ions and/or chloride ions used as counter ions of the basic substance is reduced by adjusting total ammonia concentration in the medium to be within a specific concentration range during at least a part of the total period of culture process. That is, the method of the present invention is a method for producing the basic substance in the medium in which sulfate ions and chloride ions are reduced by using such a total ammonia concentration that the total ammonia is secured in an amount required for the growth of the microorganism or the production of the objective substance as a nitrogen source, and growth of the microorganism or the production of the objective substance is not inhibited.

Examples of the specific range of the total ammonia concentration include a range satisfying the following conditions:

(A) the concentration of ammonium ions in the medium is at such a level that the sum of the ion equivalents of bicarbonate and/or carbonate ions, and other anions dissolved in the medium is larger than the ion equivalent of the basic substance ionized from the basic substance accumulated in the medium, and (B) the total ammonia concentration in the medium is at a level not inhibiting the production of the basic substance by the microorganism, which is determined beforehand as follows:

the microorganism is cultured in the medium having various pH values and various total ammonia concentrations, productivity of the basic substance is measured at each pH value and each total ammonia concentration, and a total ammonia concentration providing 50% or more of productivity of the basic substance based on the productivity obtained under optimum conditions is determined for each pH value.

Furthermore, in another embodiment of the present invention, the specific range of the total ammonia concentration is determined beforehand as follows.

(A') (Procedure 1: Evaluation of Fermentation Result Under Neutral Condition)

The culture is performed in a medium which contains an amount of sulfate and/or chloride ions which is sufficient for performing the culture at pH 7.2 or lower as a source of counter ions of the objective basic substance, of which pH is maintained to be in the range between 6.5 to 7.2 by adding at least one of ammonia gas, aqueous ammonia and urea, and productivity of the basic substance is measured, (B') (Procedure 2: Evaluation of Fermentation Results with Reduced Amount of Sulfate Ions and Chloride Ions at Various Ammonium Concentrations)

The culture is started in the same medium as that used in Procedure 1 (step A') described above except that sulfate and/or chloride ions of medium components are lower by a desired amount, and the culture is continued with various total ammonia concentrations during a period where it becomes impossible to maintain the pH of the medium to be 7.2 or lower due to shortage of sulfate ions and/or chloride ions as counter ions of the basic substance caused with accumulation of the objective basic substance to determine a total ammonia concentration range providing 50% or more of productivity based on the productivity measured in the step (A').

Moreover, in another embodiment of the present invention, when the specific range of total ammonia concentration is not determined beforehand, the total ammonia concentration can be adjusted to be within the predetermined range. Specifically, the total ammonia concentration in the medium is adjusted by adding ammonia or urea to the medium when activity of the microorganism is reduced or ceases as determined on the basis of dissolved oxygen concentration in the medium, consumption rate of carbon source in the medium, turbidity of the medium, productivity of the basic substance, and the pH change in the medium observed as indexes. The medium has the same composition as that of a medium containing sulfate ions and/or chloride ions as a counter ion source of the basic substance in an amount sufficient for performing the culture at pH 7.2 or lower except that amount of sulfate ions and/or chloride ions is reduced by a desired amount. Examples of the at least a part of the total period include a period when the pH of the medium cannot be maintained to be 7.2 or lower due to shortage of counter ions for the basic substance which has accumulated in the medium.

Examples of the other anions include chloride ions, sulfate ions, phosphate ions, ions of organic acids (acetic acid, lactic acid, succinic acid etc.), and so forth. Furthermore, bicarbonate ions and/or carbonate ions dissolved in the medium function as counter anions of the basic substance.

In the present invention, an ion equivalent is a value obtained by multiplying the molar concentration of each ion by the ion's valence, and it is represented in a unit of eq/l. That is, the ion equivalent of 1 mM of a monovalent ion is 1 meq/l, and the ion equivalent of 1 mM of a divalent ion is 2 meq/l.

The aforementioned total ammonia concentration is adjusted in order to make the total ammonia exist in the medium in an amount required for growth of the microorganism or the production of the basic substance, and at a concentration not inhibiting the production of the basic substance by the microorganism, and the medium is thereby automatically adjusted to a pH suitable for dissolving bicarbonate ions and/or carbonate ions required as counter anions of the basic substance.

In the present invention, "the total ammonia" means the sum of non-dissociated ammonia ($NH_3$) and ammonium ions ($NH_4^+$). When adjusting the total ammonia concentration, non-dissociated ammonia or ammonium ions may be measured, or the both may be measured.

Typically, ammonium sulfate and ammonium chloride are added to the medium as sources of counter anions of the basic substance and source of nitrogen, in general. Moreover, since ammonia and urea are typically used to adjust the pH of the medium, high concentration of ammonia and ammonium ions are present in the medium. When reducing the amount of ammonium sulfate or ammonium chloride in order to reduce the amount of sulfate or chloride ions added to the medium, a nitrogen source such as ammonia is supplied in an amount corresponding to the amount to be reduced. For such an operation, it has been necessary to develop a method for supplying ammonia, which takes into consideration the balance between cations including those produced by bacteria and increasing with progress of the culture such as those of the objective basic substance, cations which ionize from added ammonia, cations added to the medium such as sodium and potassium ions, and so forth, and anions increasing in the medium due to generation by respiration of bacteria or addition to the medium. If this balance is not maintained, the fermentation will not progress, because the ammonia concentration will become unduly high, or the pH will become excessively high, or conversely, ammonia could become depleted. According to the present invention, development of a method for adding ammonia for adjusting the total ammonia concentration to be within a specific range can enable favorable maintenance of the aforementioned balance of cations and anions, and thus favorable growth of a microorganism and favorable generation of a basic substance can be realized even under a condition that the amount of sulfate ions and chloride ions present in the medium is reduced.

The total ammonia concentration in the medium is adjusted by adding at least one of ammonia gas, ammonia solution and urea to the medium so that the total ammonia concentration in the medium is at an acceptable level. Furthermore, an ammonium salt such as ammonium chloride or ammonium sulfate may also be added, unless detrimental to the effect of the invention. Moreover, an ammonium salt containing bicarbonate ion or carbonate ion as a counter ion, which can be easily removed as a gas after completion of the culture, may also be used. The total ammonia concentration can be adjusted by using measured values of ammonium ion or ammonia concentration in the medium or exhaust gas as an index. Moreover, it is also possible to adjust the total ammonia concentration by determining beforehand a pH providing an acceptable total ammonia concentration when pH is adjusted with ammonia and adding ammonia so that such a pH can be obtained. In such a case, pH determined as described above may be changed during the culture, if needed.

Moreover, the total ammonia concentration in the medium can also be adjusted by adding ammonia or urea to the medium when the activity of the microorganism is reduced or ceases as determined on the basis of dissolved oxygen concentration in the medium, consumption rate of carbon source in the medium, turbidity of the medium, productivity of the basic substance, and the change in pH in the medium observed as indexes. That is, if the nitrogen source in the medium runs short or is depleted, proliferation of the microorganism or the activity of the microorganism, such as production of an objective substance is reduced or ceases. Activity of a microorganism usually appears as consumption of dissolved oxygen and a carbon source in a medium, increase of turbidity of medium, production of an objective substance, and reduction in the pH of the medium due to the consumption of ammonia or the release of carbon dioxide by respiration. Therefore, when activity of a microorganism is reduced or ceases, the concentration of dissolved oxygen in a medium increases when aeration and stirring rates per unit time are constant, and pH of a medium increases due to a decrease in the consumption of ammonia and secretion of carbon dioxide. Furthermore, the consumption rate of a carbon source, increasing rate of turbidity of a medium and the production rate of an objective substance are reduced. Therefore, when stagnation of activity of a microorganism is observed on the basis of these items used as indexes under a state that medium components other than a nitrogen source are sufficient, the nitrogen source runs short or has been depleted. If this occurs, ammonia or urea is added to the medium in an amount which is required for the growth of the microorganism or the production of the objective substance. By repeating this procedure, the total ammonia concentration in the medium is maintained to be within a specific range as a result. If the culture is performed with adding urea to the medium, urea is utilized by the microorganism, and ammonia is released into the medium. If the addition of ammonia or urea is repeated as described above, the pH of the medium gradually increases. The amount of ammonia or urea added at each time point may be, for example, 300 mM, preferably 200 mM, more preferably 100 mM, expressed as the final concentration of total ammonia in the medium. Alternatively, ammonia or urea may be added so that the pH increases by 0.3 or less, preferably 0.15 or less, more preferably 0.1 or less, after addition of ammonia or urea.

The dissolved oxygen concentration in the medium can be measured, for example, by using a dissolved oxygen electrode.

Whether the sum of the ion equivalents of bicarbonate ions and/or carbonate ions and the other anions, which are all dissolved in the medium is higher than the ion equivalent of the basic substance which has accumulated in the medium can be confirmed by measuring the concentrations of bicarbonate ions, carbonate ions and other anions as well as the concentration of the basic substance. Moreover, the above conditions can also be fulfilled by conducting a preliminary experiment to determine the pH and/or the addition amount of ammonia which satisfies the aforementioned conditions, and performing the culture at the pre-determined pH and/or addition of pre-determined amount of ammonia.

In the present invention, the pH of the culture may or may not be constant. Moreover, when the pH of the medium is controlled, it may be controlled by using pH itself as an index, or indirectly by controlling the total ammonia concentration without directly controlling the pH. Furthermore, if ammonia or urea is added using the activity of the microorganism as an index as described above, the total ammonia concentration in the medium is adjusted so that it is within an appropriate concentration range, and the pH gradually increases with the accumulation of the basic substance. Moreover, if the culture is performed with controlling the total ammonia concentration to be within a specific range, the pH changes as a result of change of accumulation balance of various cations and anions in the medium. Whichever means is chosen, the total ammonia concentration in the medium is adjusted to be within a specific concentration range as a result, and thus the amount of sulfate ions and/or chloride ions used as counter ions of the basic substance can be reduced.

In the present invention, the expression "not inhibiting production of a basic substance" means that the microorganism used for the present invention grows favorably, and the basic substance is favorably produced. When the growth of the microorganism is insufficient, or when the basic substance is not efficiently produced in spite of favorable growth of the microorganism, it is considered that production of the basic substance is inhibited.

Specifically, the microorganism used for the present invention is cultured at various pH levels and the total ammonia concentrations of the medium, productivities of the basic substance accumulated in the medium are measured, and the total ammonia concentrations which results in production of the basic substance at a rate of preferably 50% or more, more preferably 70% or more, particularly preferably 90% or more, as compared to the amount of the basic substance obtainable under optimal conditions, for example, conventionally used general conditions at a neutral pH, at each pH value are considered to be concentrations "not inhibiting production of the basic substance". In the present invention, "productivity" refers to the yield, the production rate or the total amount produced. The "yield" refers to production amount of the basic substance based on the carbon source present in the medium which is able to be consumed, and the "production rate" refers to a production amount per unit time. Moreover, when the term "production amount" or "amount produced" is solely used, it refers to the amount of the basic substance which is accumulated in the medium once the carbon source is completely consumed.

Alternatively, the microorganism used for the present invention is cultured under optimal conditions, for example, conventionally used general conditions at a neutral pH, and productivity of the basic substance which has accumulated in the medium is measured. Then, the culture is performed in a medium having the same composition except that amount of sulfate ions and/or chloride ions is reduced by a desired amount, and the productivity of the basic substance is measured. In this case, there is a period where the pH of the medium will increase due to the shortage of sulfate ions and/or chloride ions as the counter ions with accumulation of the objective basic substance. For that period, the culture is performed with maintaining the total ammonia concentration to be within the specific concentration range. As for the range within which the concentration is controlled, the culture is performed with various concentrations within the range of 1 to 500 mM, and concentrations within a range providing a productivity of the basic substance of preferably 50% or more, more preferably 70% or more, particularly preferably 90% or more, of the productivity obtainable under optimal conditions are determined to be concentrations "not inhibiting production of the basic substance". Examples of the medium used for the aforementioned "conventionally used general conditions at a neutral pH" include a medium containing sulfate ions and/or chloride ions in an amount sufficient for performing the culture at pH 7.2 or lower.

The desired amount by which the sulfate ions and/or chloride ions are reduced is not particularly limited, so long as objective productivity of the basic substance can be obtained.

The total ammonia concentration which is defined as "not inhibiting the production of the basic substance" can also be determined, for example, as follows. The microorganism used for the present invention is cultured at various pH levels and the total ammonia concentration of the medium, and the amount of the basic substance which accumulates in the medium are measured. The accumulated amount of the basic substance which is obtained under various conditions are compared with the amount accumulated under the optimum conditions. Thus, the total ammonia concentration which does not inhibit the production of the basic substance can be determined. The optimum conditions are defined as conditions of culture using sufficient counter ions at a neutral pH as in the typically used general conditions at a neutral pH.

Furthermore, another method for determining the total ammonia concentration which is defined as "not inhibiting production of the basic substance" is, for example, as follows. The microorganism used for the present invention is cultured under optimal conditions, for example, typically used general conditions at a neutral pH, and productivity of the basic substance which accumulates in the medium is measured. Then, the culture is performed in a medium having the same composition except that sulfate ions and/or chloride ions is reduced by a desired amount, and the productivity is examined. In this case, there is a period where pH of the medium will increase due to shortage of sulfate ions and/or chloride ions as the counter ions with accumulation of the objective basic substance. For that period, the culture is performed with maintaining the total ammonia concentration to be within the specific concentration range. As for the range within which the concentration is controlled, the culture is performed with various concentrations within the range of 1 to 500 mM, and the productivities obtained thereby are compared to that under the optimum conditions.

The concentration which is defined as "not inhibiting production of the basic substance" includes, for example, a concentration allows production of the basic substance preferably at 50% or more, more preferably 70% or more, particularly preferably 90% or more, as compared to the productivity of the basic substance under optimal conditions. Specifically, the total ammonia concentration in the medium is, for example, preferably 300 mM or less, more preferably 200 mM or less, particularly preferably 100 mM or less. The degree to which ammonia dissociates is reduced as the pH increases. Non-dissociated ammonia is more toxic to bacteria as compared with ammonium ion. Therefore, the upper limit of the total ammonia concentration also depends on the pH of the medium. That is, as the pH of the medium increases, the acceptable total ammonia concentration becomes lower. Therefore, as for the aforementioned total ammonia concentration which is defined as "not inhibiting production of the basic substance", a total ammonia concentration range acceptable for the highest pH during the culture may be regarded as the total ammonia concentration range throughout the culture.

On the other hand, the total concentration of ammonia as a nitrogen source, which is required for growth of the microorganism and production of the basic substance, is not particularly limited, so long as the productivity of the objective substance provided by the microorganism is not reduced due to a shortage of the nitrogen source during the culture, and it may be appropriately determined. For example, the ammonia concentration is measured over time during the culture, and when the ammonia in the medium is depleted, a small amount of ammonia may be added to the medium. Although the concentration after the addition of ammonia is not particularly limited, it is, for example, preferably 1 mM or higher, more preferably 5 mM or higher, particularly preferably 10 mM or higher, in terms of the total ammonia concentration.

The method of the present invention may include a culture step which is primarily for proliferating the microorganism having an ability to produce a basic substance, and a culture step which is primarily for allowing the microorganism to produce the basic substance. Furthermore, in the method of the present invention, proliferation of the microorganism and production of the basic substance may be performed in parallel. Furthermore, besides such culture as described above, which may also be called main fermentation, main culture or the like, a preculture may also be independently performed.

In the present invention, in addition to adjusting the total ammonia concentration in the medium as described above, an operation facilitating dissolution of bicarbonate ions and/or carbonate ions in the medium may also be performed. Examples of such an operation include controlling the pressure in the fermentation tank during the culture so that it is positive, supplying carbon dioxide gas or a mixed gas containing carbon dioxide gas to the medium, limiting the aeration in the fermentation tank so that bicarbonate ions and/or carbonate ions are dissolved in the medium, increasing the pH of the medium by adding cations other than ammonium ions such as sodium ions and potassium ions to the medium, and so forth.

To make the pressure in the fermentation tank positive, for example, the pressure of the air supply to the fermentation tank may be made higher than the pressure of the exhaust. By making the pressure in the fermentation tank higher, carbon dioxide gas generated by the fermentation dissolves in the culture medium and produces bicarbonate ions or carbonate ions. Specifically, the pressure in the fermentation tank may be 0.13 to 0.3 MPa, preferably 0.15 to 0.25 MPa.

Furthermore, carbon dioxide gas may be dissolved in the culture medium by supplying carbon dioxide gas or a mixed gas containing carbon dioxide gas into the medium. Alternatively, by limiting aeration to the fermentation tank, carbon dioxide gas generated by the fermentation can also dissolves in the medium. A suitable aeration rate can be determined by, for example, measuring the amount of bicarbonate ions or carbonate ions in the medium, or measuring the pH and ammonia concentration of the medium. When carbon dioxide gas is supplied to the medium, for example, pure carbon dioxide gas or a mixed gas containing 5% by volume or more of carbon dioxide gas may be bubbled into the medium. The aforementioned methods for dissolving bicarbonate ions and/or carbonate ions in the medium may be used independently or as a combination of two or more.

The operation of adjusting the total ammonia concentration in the medium and the operation of facilitating dissolution of bicarbonate ions and/or carbonate ions in the medium if needed may be performed during at least a part of the total period of culture process.

Although the "at least a part of the total period" is not particularly limited so long as desired productivity is obtained, it may be specifically, for example, 1/10 or more, preferably 1/5 or more, of the total culture process of the main culture. More specifically, examples of the period include a period where the pH of the medium increases due to the shortage of the counter ions such as sulfate ions and/or chloride ions, with accumulation of the objective basic substance, or a period where the pH of the medium increases due to addition of cations, or both of these periods.

The medium used for the present invention is not particularly limited, so long as at least the total ammonia concentration can be made to be within the aforementioned range by the operation of adjusting the total ammonia concentration, and a medium containing organic and inorganic nutrients such as a carbon source and a nitrogen source and other trace amount nutrients may be suitably used depending on the microorganism to be used.

Any carbon source can be used, as long as it can be consumed by the microorganism, and examples include saccharides such as saccharose, glucose, fructose, molasses and starch hydrolysate, organic acids such as acetic acid, alcohols such as ethanol, and hydrocarbons such as methane.

Examples of the nitrogen source include inorganic substances such as ammonia, protein hydrolysates, yeast extract, and so forth. Examples of the trace amount nutrients include amino acids, vitamins, and trace metal elements.

Examples of anions other than bicarbonate ions and/or carbonate ions which are present in the medium include chloride ions, sulfate ions, phosphate ions, ionized organic acids, hydroxide ions, and so forth. The sum of the ion equivalents of these other ions is usually 900 meq/l or less, preferably 700 meq/l or less, more preferably 500 meq/l or less, still more preferably 300 meq/l or less, particularly preferably 200 meq/l or less.

One of the objects of the present invention is to reduce the amount of sulfate ions and/or chloride ions used, and the ion equivalent of sulfate ions or chloride ions, or the sum of ion equivalents of these ions present in the medium is usually 700 meq/l or less, preferably 500 meq/l or less, more preferably 300 meq/l or less, still more preferably 200 meq/l or less, particularly preferably 100 meq/l or less.

The fermentation scheme is not particularly limited, and may be a batch culture in which medium is not fed, a feeding culture in which the medium is fed after the charged sugar is consumed, a continuous culture in which the medium is extracted when the volume of the medium exceeds the volume acceptable for a fermentation tank, a cell recycle method in which bacterial cells are recycled, and so forth. The culture temperature may be appropriately determined depending on the chosen microorganism. It is usually 25 to 45° C., preferably 30 to 40° C. Furthermore, it is preferable to stir sufficiently so that sufficient oxygen is present during the fermentation.

The culture for producing the objective basic substance is specifically performed, for example, as follows. A medium containing typical medium components is prepared, but most if not all of the ammonium salts such as ammonium sulfate and ammonium chloride are eliminated. A microorganism which has been separately cultured is inoculated into this medium, and cultured while controlling the total ammonia concentration to be within a range suitable for the chosen microorganism, which is determined as described above. The ammonia concentration in the medium in the fermentation tank or the sampled medium can be measured by using, for example, a commercially available ion meter or the like. By using the measured values as an index, the total ammonia concentration can be controlled. To maintain the total ammonia concentration within the predetermined concentration range, ammonia gas, aqueous ammonia or urea may be added to the medium. The total ammonia concentration in the medium can also be indirectly measured by measuring the ammonia concentration in the exhaust gas from the fermentation tank using a common ammonia electrode.

Furthermore, in the present invention, the total ammonia concentration in the medium can be adjusted by the following method using the pH of the medium as an index, as described above.

The culture is performed in a medium which has the same composition as a medium containing sulfate ions and/or chloride ions in an amount sufficient to maintain the culture at pH 7.2 or lower, except that amount of sulfate ions and/or chloride ions is reduced by a desired amount at various pH levels, wherein the pH level is changed by adding at least any one of ammonia gas, aqueous ammonia and urea, and the culture is continued while maintaining the total ammonia concentration in the medium so that it is within the preferred concentration range by adding at least any one of ammonia gas, aqueous ammonia and urea to the medium based on indicators such as change in the dissolved oxygen concentration in the medium, the change in the consumption rate of the carbon source in the medium, the change in the turbidity of the medium, the pH change in the medium, or the like in an indirect manner during a period where pH of the medium cannot be maintained at 7.2 or lower due to shortage of counter ions to the basic substance which has accumulated in the medium.

Examples of the basic substance produced by the method of the present invention include basic amino acids, specifically, L-lysine, L-arginine and L-histidine. Among these, L-lysine is preferred.

The microorganism which is able to produce a basic substance is not particularly limited, and any microorganism can be chosen so long as it can produce the basic substance by fermentation. In particular, a microorganism which favorably produces the basic substance even at a high pH of medium, if the total ammonia concentration of the medium is low, is preferably chosen. Examples of such a microorganism include bacteria belonging to coryneform bacteria, genus *Escherichia*, *Serratia*, or *Bacillus*.

Coryneform bacteria and *Escherichia* bacteria will be explained hereinafter, however, the microorganism used for the method of the present invention is not limited to these bacteria.

The coryneform bacteria used for the present invention include *Corynebacterium* bacteria and those bacteria having been previously classified into the genus *Brevibacterium* but have been re-classified into the genus *Corynebacterium* (Int. J. Syst. Bacteriol., 41, 255 (1981)), and further include bacteria belonging to the genus *Brevibacterium*, which is extremely close to the genus *Corynebacterium*. Specific examples include the following:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium efficiens*
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*

*Brevibacterium album*
*Brevibacterium cerinum*
*Microbacterium ammoniaphilum*
Specifically, the following strains are included:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* (*Corynebacterium glutamicum*) ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067
*Brevibacterium immariophilum* ATCC 14068
*Brevibacterium lactofermentum* (*Corynebacterium glutamicum*) ATCC 13665, ATCC 13869
*Brevibacterium roseum* ATCC 13825
*Brevibacterium saccharolyticum* ATCC 14066
*Brevibacterium thiogenitalis* ATCC 19240
*Brevibacterium ammoniagenes* (*Corynebacterium ammoniagenes*) ATCC 6871
*Brevibacterium album* ATCC 15111
*Brevibacterium cerinum* ATCC 15112
*Microbacterium ammoniaphilum* ATCC 15354

Examples of the *Escherichia* bacteria include *Escherichia coli*. When *Escherichia coli* is bred by using genetic engineering techniques, the *E. coli* K12 strain and derivatives thereof, i.e., *E. coli* MG1655 strain (ATCC No. 47076), W3110 strain (ATCC No. 27325), and so forth, may be chosen. The *E. coli* K12 strain was isolated at Stanford University in 1922, and is a lysogenic bacterium of λ phage. In addition, it is a highly versatile strain having the F-factor, for which genetic recombinants can be created by conjugation or the like. Furthermore, the genomic sequence of the *E. coli* K12 strain has been determined, and the genetic information is publicly available. The *E. coli* K12 strain and derivatives thereof may be obtained from American Type Culture Collection (ATCC, Address: P.O. Box 1549, Manassas, Va. 20108, United States of America).

Examples of coryneform bacteria which are able to produce L-lysine include S-(2-aminoethyl)cysteine (abbreviated as "AEC" hereinafter) resistant mutant strains, mutant strains which require an amino acid such as L-homoserine for growth (Japanese Patent Publication (Kokoku) Nos. 48-28078 and 56-6499), mutant strains with resistance to AEC and which further require an amino acid such as L-leucine, L-homoserine, L-proline, L-serine, L-arginine, L-alanine and L-valine (U.S. Pat. Nos. 3,708,395 and 3,825,472), L-lysine producing mutant strains with resistance to DL-α-amino-ε-caprolactam, α-amino-lauryllactam, aspartic acid analogue, sulfa drug, quinoid and N-lauroylleucine, L-lysine producing mutant strains with resistance to oxaloacetate decarboxylase or a respiratory tract enzyme inhibitor (Japanese Patent Laid-open Nos. 50-53588, 50-31093, 52-102498, 53-9394, 53-86089, 55-9783, 55-9759, 56-32995, 56-39778, Japanese Patent Publication Nos. 53-43591 and 53-1833), L-lysine producing mutant strains which require inositol or acetic acid (Japanese Patent Laid-open Nos. 55-9784 and 56-8692), L-lysine producing mutant strains that are susceptible to fluoropyruvic acid or a temperature of 34° C. or higher (Japanese Patent Laid-open Nos. 55-9783 and 53-86090), L-lysine producing mutant strains of *Brevibacterium* or *Corynebacterium* bacteria with resistance to ethylene glycol (U.S. Pat. No. 333,455), and so forth.

Specific examples include, for example, the *Brevibacterium lactofermentum* ATCC 31269, *Brevibacterium flavum* ATCC 21475, and *Corynebacterium acetoglutamicum* ATCC 21491 strains.

Furthermore, the *Brevibacterium lactofermentum* ATCC 13869/pVK-C*, plysE strain described in the examples is also a preferred L-lysine producing coryneform bacterium. This strain was obtained by incorporating a plasmid pVK-C* containing the gene coding for aspartokinase which is desensitized to feedback inhibition by L-lysine and L-threonine (lysC*) and a plasmid plysE (U.S. Patent Application No. 2003113899) containing the lysE gene which is homologous to the gene which promotes secretion of L-lysine known for the *Corynebacterium* bacteria (International Patent Publication 9723597A2) into the ATCC 13869 strain, which is a wild type strain of *Brevibacterium lactofermentum*.

The lysC* gene can be isolated from, for example, the L-lysine producing mutant strain AJ3463 (FERM P-1987) (see Japanese Patent Publication No. 51-34477) which is generated by mutagenesis of the ATCC 13869 strain. The AJ3463 strain was deposited at International Patent Organism Depositary, National Institute of Advanced Industrial Science and Technology (formerly National Institute of Bioscience and Human-Technology, Agency of Industrial Science and Technology, Address: Tsukuba Central 6, 1-1, Higashi 1-Chome, Tsukuba-shi, Ibaraki-ken, 305-8566, Japan) on Mar. 22, 1973, and assigned accession number FERM P-1987. Furthermore, a lysC* gene fragment can also be isolated from the *Brevibacterium lactofermentum* AJ12691 strain which contains a plasmid p399AK9B containing the gene. The AJ12691 strain was deposited at International Patent Organism Depositary, National Institute of Advanced Industrial Science and Technology on Apr. 10, 1992, and assigned accession number FERM P-12918. Then, it was converted to an international deposit under the provisions of the Budapest Treaty on Feb. 10, 1995, and assigned accession number FERM BP-4999. The plasmid p399AK9B (U.S. Pat. No. 5,766,925) was obtained by inserting a DNA fragment enabling autonomous replication of the plasmid in *Corynebacterium* bacteria into a plasmid p399AK9 which was obtained by inserting lysC derived from the AJ3463 strain into the cloning vector pHSG399 (see Takeshita, S et al, Gene (1987), 61, 63-74).

In the aforementioned desensitized aspartokinase, the alanine residue at position 279 of the α-subunit and the alanine residue at position 30 the β-subunit of the wild-type aspartokinase are each replaced with a threonine residue. The α-subunit and the β-subunit are both encoded in the same frame of the lysC gene. The nucleotide sequence of the lysC* gene and the amino acid sequence of the α-subunit of the desensitized aspartokinase are shown in the sequence listing as SEQ ID NOS: 5 and 6, respectively, and the nucleotide sequence of the same gene and the amino acid sequence of the β-subunit of the desensitized aspartokinase are shown as SEQ ID NOS: 7 and 8, respectively.

The lysE gene of coryneform bacteria can be obtained by PCR (polymerase chain reaction, see White, T. J. et al., Trends Genet., 5, 185 (1989)) using primers based on the reported nucleotide sequence (GenBank accession X96471), for example, primers shown as SEQ ID NOS: 3 and 4, and a chromosomal DNA of coryneform bacterium as the template. A nucleotide sequence of a DNA fragment containing the *Corynebacterium glutamicum* lysG and lysE genes (Gen- Bank accession X96471) is shown as SEQ ID NO: 10, and the amino acid sequence of the LysE protein encoded by this gene is shown as SEQ ID NO: 9. LysG is encoded by a complementary sequence corresponding to the nucleotide numbers 1723 to 2352 in SEQ ID NO: 8.

The DNAs coding for the α-subunit, β-subunit and LysE protein of aspartokinase include DNAs coding for proteins that may include deletions, substitutions, insertions or additions of one or several amino acid residues at one or several positions in each protein, provided that the activities of the proteins are not lost. Although the number of amino acid residues meant by the term "several" may vary depending on the positions in the three dimensional structures of the proteins and types of amino acid residues, it is preferably 2 to 30, more preferably 2 to 20, particularly preferably 2 to 10, for each protein. This is based on the following reasons. That is, it is because some amino acids are highly homologous to each other, and the differences among such amino acids do not greatly affect the three dimensional structures and activities of proteins. Therefore, each protein may be one having a homology of 50% or more, preferably 70% or more, more preferably 90% or more, particularly preferably 95% or more, to the amino acid residues of SEQ ID NO: 6, 8 or 10 and having the activity of aspartokinase or LysE protein.

Such modification of the proteins as described above is a conservative mutation that maintains the activity of each protein. The substitution is a change in which at least on residue in an amino acid sequence is removed, and another residue is inserted there. Examples of substitution of an amino acid residue for an original amino acid residue considered as a conservative substitution include substitution of ser or thr for ala, substitution of gln, his or lys for arg, substitution of glu, gln, lys, his or asp for asn, substitution of asn, glu or gln for asp, substitution of ser or ala for cys, substitution of asn, glu, lys, his, asp or arg for gln, substitution of asn, gln, lys or asp for glu, substitution of pro for gly, substitution of asn, lys, gln, arg or tyr for his, substitution of leu, met, val or phe for ile, substitution of ile, met, val or phe for leu, substitution of asn, glu, gln, his or arg for lys, substitution of ile, leu, val or phe for met, substitution of trp, tyr, met, ile or leu for phe, substitution of thr or ala for ser, substitution of ser or ala for thr, substitution of phe or tyr for trp, substitution of his, phe or trp for tyr, and substitution of met, ile or leu for val.

A DNA coding for substantially the same protein as the protein having the amino acid sequence as shown in SEQ ID NOS: 6, 8 or 10 can be obtained by modifying the nucleotide sequence coding for the amino acid sequence as shown in SEQ ID NOS: 6, 8 or 10 by using, for example, site-specific mutagenesis, so that substitution, deletion, insertion or addition of one or several amino acid residues occurs. Such a modified DNA can be obtained in a conventional manner by treating with a regent or under conditions which cause a mutation. Examples of such a treatment include treating the DNA coding for the protein of the present invention with hydroxylamine, ultraviolet ray irradiation of a microorganism containing the DNA, treating with a regent such as N-methyl-N'-nitro-N-nitrosoguanidine or nitrous acid.

A DNA coding for such a modified protein as described above can also be obtained by isolating a DNA which is able to hybridize with the lysC gene, lysE gene or a portion of these genes under stringent conditions and still encodes a protein having aspartokinase activity or the activity of the LysE protein. The term "stringent conditions" includes a condition when a so-called specific hybrid is formed, and non-specific hybrid is not formed. The stringent conditions include, for example, conditions under which DNAs having high homology to each other, for example, DNAs having a homology of not less than 70%, preferably not less than 80%, more preferably not less than 90%, particularly preferably not less than 95%, are able to hybridize. The stringent conditions also include typical washing conditions of Southern hybridization, i.e., 1×SSC, 0.1% SDS, preferably 0.1×SSC, 0.1% SDS, at 60° C.

Examples of L-lysine producing bacteria belonging to the genus Escherichia include mutants having resistance to L-lysine analogues. The L-lysine analogue inhibits growth of Escherichia bacteria, but this inhibition is fully or partially eliminated when L-lysine coexists in a medium. Examples of L-lysine analogues include oxalysine, lysine hydroxamate, (S)-(2-aminoethyl)-L-cysteine (AEC), γ-methyllysine, α-chlorocaprolactam, and so forth. Mutants having resistance to these lysine analogues can be obtained by subjecting Escherichia microorganisms to a conventional artificial mutation treatment. Specific examples of bacterial strains used for producing L-lysine include E. coli AJ11442 (FERM BP-1543, NRRLB-12185; see Japanese Patent Laid-open No. 56-18596 and U.S. Pat. No. 4,346,170) and E. coli VL611 strains. The AJ11442 strain was deposited at International Patent Organism Depositary, National Institute of Advanced Industrial Science and Technology (formerly National Institute of Bioscience and Human-Technology, Agency of Industrial Science and Technology, Address: Tsukuba Central 6, 1-1, Higashi 1-Chome, Tsukuba-shi, Ibaraki-ken, 305-8566, Japan) on May 1, 1981, and assigned accession number FERM P-5084. Then, this deposit was converted to an international deposit under the provisions of the Budapest Treaty on Oct. 29, 1987, and assigned accession number FERM BP-1543. In these microorganisms, feedback inhibition of aspartokinase by L-lysine is desensitized.

Furthermore, for example, bacteria with enhanced expression of a gene coding for an enzyme involved in L-lysine biosynthesis other than desensitized aspartokinase may also used as a preferred L-lysine producing bacteria. Examples of such an enzyme include enzymes involved in the diaminopimelate pathway, such as dihydrodipicolinate synthase, dihydrodipicolinate reductase, diaminopimelate decarboxylase, diaminopimelate dehydrogenase (International Patent Publication WO96/40934 for all of the foregoing enzymes), phosphoenolpyruvate carboxylase (Japanese Patent Laid-open No. 60-87788), aspartate aminotransferase (Japanese Patent Publication No. 6-102028), diaminopimelate epimerase (Japanese Patent Laid-open No. 2003-135066), and aspartate semialdehyde dehydrogenase (International Patent Publication WO00/61723), enzymes involved in the aminoadipate pathway, such as homoaconitate hydratase (Japanese Patent Laid-open No. 2000-157276), and so forth.

Specific examples of E. coli strains having L-lysine producing ability include the E. coli W3110(tyrA)/pCABD2 strain (International Patent Publication WO95/16042) and so forth. The E. coli W3110(tyrA)/pCABD2 strain was obtained by introducing the plasmid pCABD2 containing genes encoding the L-lysine biosynthesis system enzymes into W3110(tyrA), which is a tyrA deficient strain of E. coli (it was designated as AJ12604, deposited at International Patent Organism Depositary, National Institute of Advanced Industrial Science and Technology (formerly National Institute of Bioscience and Human-Technology, Agency of Industrial Science and Technology, Address: Tsukuba Central 6, 1-1, Higashi 1-Chome, Tsukuba-shi, Ibaraki-ken, 305-8566, Japan) on Jan. 28, 1991, and assigned accession number FERM P-11975, and then the deposit was converted to an international deposit under the provisions of the Budapest Treaty on Sep. 26, 1991, and assigned accession number FERM BP-3579).

The plasmid pCABD2 contains a gene coding for a mutant dihydrodipicolinate synthase, wherein the histidine residue at position 118 is mutated to a tyrosine residue, and feedback inhibition by L-lysine is desensitized, a gene coding for a mutant aspartokinase III, wherein threonine residue at position 352 is mutated to an isoleucine residue, and feedback inhibition by L-lysine is desensitized, and genes coding for dihydrodipicolinate reductase and diaminopimelate dehydrogenase.

Furthermore, the *E. coli* W3110(tyrA) strain can be obtained as described below. That is, many strains obtained by introducing a plasmid into the W3110(tyrA) strain are disclosed in European Patent Laid-open Publication No. 488424/1992. For example, a strain obtained by introducing a plasmid pHATerm was designated as *E. coli* W3110(tyrA)/pHATerm strain, and deposited at the National Institute of Bioscience and Human-Technology, Agency of Industrial Science and Technology, and assigned accession number FERM BP-3653. The W3110(tyrA) strain can be obtained by, for example, eliminating the plasmid pHATerm from that *E. coli* W3110(tyrA)/pHATerm strain. Elimination of the plasmid can be performed in a conventional manner.

Furthermore, the WC196 strain (see International Patent Publication WO96/17930) can also be used as an L-lysine producing strain of *E. coli*. The WC196 strain was bred by imparting AEC (S-(2-aminoethyl)cysteine) resistance to the W3110 strain derived from *E. coli* K-12. This strain was designated *E. coli* AJ13069, and deposited at the National Institute of Bioscience and Human-Technology, Agency of Industrial Science and Technology (presently International Patent Organism Depositary, National Institute of Advanced Industrial Science and Technology (Tsukuba Central 6, 1-1, Higashi 1-Chome, Tsukuba-shi, Ibaraki-ken, 305-8566, Japan)) on Dec. 6, 1994, and assigned accession number FERM P-14690. Then, the deposit was converted to an international deposit under the provisions of the Budapest Treaty on Sep. 29, 1995, and assigned accession number FERM BP-5252.

The microorganism usable for the present invention may have decreased activity of an enzyme that catalyzes a reaction for generation of compounds other than L-lysine via pathway which branches off of the biosynthetic pathway of L-lysine, or an enzyme which down regulates L-lysine production, or may be deficient in such an enzyme. Illustrative examples of the enzyme involved in L-lysine production include homoserine dehydrogenase, lysine decarboxylase (cadA, ldcC) and malic enzyme. Strains in which the activities of these enzymes are decreased or deficient are described in International Patent Publications WO95/23864, WO96/17930, WO2005/010175, and so forth.

To reduce or eliminate enzymatic activities, genes encoding the enzymes on a chromosome may be mutated by a common mutagenesis method so that intracellular activities of the enzymes are reduced or eliminated. For example, this can be achieved by using genetic recombination to eliminate these genes coding for the enzymes on a chromosome or to modify an expression control sequence, such as a promoter or the Shine-Dalgarno (SD) sequence. It can also be achieved by introducing an amino acid substitution (missense mutation), introducing a stop codon (nonsense mutation), introducing a frame shift mutation adding or deleting one or two nucleotides into coding regions for the enzymes on the chromosome, or deleting a part of the genes (Journal of Biological Chemistry, 272:8611-8617 (1997)). The enzymatic activities can also be decreased or eliminated by constructing a gene which encodes a mutant enzyme, wherein the coding region is deleted, and replacing the wild type gene on the chromosome by homologous recombination or the like with the mutated gene, or introducing a transposon or IS factor into the gene.

For example, the following methods may be employed to introduce a mutation which causes a decrease in the activities of the aforementioned enzymes or eliminates the activities by genetic recombination. The objective gene on a chromosome can be replaced with a mutant gene which cannot produce an enzyme that normally functions by modifying a partial sequence of the objective gene to prepare the mutant gene, and transforming a coryneform bacterium with a DNA containing the mutant gene to cause recombination between the mutant gene and the gene on the chromosome. Such site-specific mutagenesis based on gene substitution using homologous recombination has been already established, and methods using linear DNA, methods using plasmids containing a temperature-sensitive replication origin (Proc. Natl. Acad. Sci. USA, 2000, vol. 97, No. 12, pp. 6640-6645; U.S. Pat. No. 6,303,383; Japanese Patent Laid-open No. 05-007491) and so forth, are known. Furthermore, such site-specific mutagenesis based on gene substitution using homologous recombination as described above can also be performed with a plasmid which is not able to replicate in the host.

Furthermore, microorganisms which have been modified so that expression amount of the L-lysine and L-arginine secretion gene, ybjE, is increased can also be used for the present invention (International Patent Publication WO2005/073390).

Examples of L-lysine producing bacteria belonging to the genus *Serratia* include *Serratia* bacteria transformed with a DNA coding for dihydrodipicolinate synthase which has a mutation that desensitizes feedback inhibition by L-lysine, and *Serratia* bacteria containing aspartokinase which is desensitized to feedback inhibition by L-lysine (International Patent Publication WO96/41871).

Examples of coryneform bacteria which produce L-arginine include wild-type strains of coryneform bacteria: coryneform bacteria resistant to certain agents including sulfa drugs, 2-thiazolealanine, α-amino-β-hydroxyvaleric acid and so forth: coryneform bacteria exhibiting auxotrophy for L-histidine, L-proline, L-threonine, L-isoleucine, L-methionine or L-tryptophan in addition being resistant to 2-thiazolealanine (Japanese Patent Laid-open No. 54-44096); coryneform bacteria resistant to ketomalonic acid, fluoromalonic acid, or monofluoroacetic acid (Japanese Patent Laid-open No. 57-18989); coryneform bacteria resistant to argininol (Japanese Patent Laid-open No. 62-24075); coryneform bacteria resistant to X-guanidine (X represents a derivative of fatty acid or aliphatic chain, Japanese Patent Laid-open No. 2-186995) and so forth. Furthermore, the coryneform bacteria which are deficient in the L-arginine repressor (U.S. Patent Application No. 20020045233), and the coryneform bacteria with increased glutamate dehydrogenase activity (European Patent Publication Laid-open No. 1057893) are also suitable strains for L-arginine production.

Specifically, the examples include the *Brevibacterium flavum* AJ11169 (FERM BP-6892), *Corynebacterium glutamicum* AJ12092 (FERM BP-6906), *Brevibacterium flavum* AJ11336 (FERM BP-6893), *Brevibacterium flavum* AJ11345 (FERM BP-6894), and *Brevibacterium lactofermentum* AJ12430 (FERM BP-2228) strains. The AJ11169 and AJ12092 strains are resistant to 2-thiazolealanine (Japanese Patent Laid-open No. 54-44096). The AJ11336 strain is resistant to argininol and sulfadiazine (Japanese Patent Publication No. 62-24075). The AJ11345 strain is resistant to arginino, 2-thiazolealanine and sulfaguanidine, and is auxotrophic for histidine (Japanese Patent Publication No.

62-24075). The AJ12430 strain is resistant to octylguanidine and 2-thiazolealanine (Japanese Patent Laid-open No. 2-186995).

The *Corynebacterium glutamicum* AJ12092 was deposited at National Institute of Bioscience and Human-Technology, Agency of Industrial Science and Technology (presently International Patent Organism Depositary, National Institute of Advanced Industrial Science and Technology, Tsukuba Central 6, 1-1, Higashi 1-Chome, Tsukuba-shi, Ibaraki-ken, 305-8566, Japan) on Dec. 6, 1994, and assigned accession number FERM P-12092. Then, the deposit was converted to an international deposit under the provisions of the Budapest Treaty on Oct. 1, 1999, and assigned accession number FERM BP-6906.

Examples of *Escherichia* bacteria which are able to produce L-arginine include *E. coli* transformed with the argA gene (see Japanese Patent Laid-open No. 57-5693), and *E. coli* strain 237 (Russian Patent Application No. 2000117677), which is an L-arginine producing derivative of mutant strain which is able to assimilate an acetic acid. The 237 strain was deposited at the Russian National Collection of Industrial Microorganisms (VKPM), GNII Genetika (Address: Russia, 117545, Moscow, 1 Dorozhnyproezd, 1) on Apr. 10, 2000, and assigned number VKPM B-7925. The deposit was converted to an international deposit under the provisions of the Budapest Treaty on May 18, 2001. The *E. coli* strain 382 is a mutant which is resistant to feedback inhibition by L-arginine (Japanese Patent Laid-open No. 2002-017342), which is a derivative of the 237 strain, and can also be employed. The *E. coli* 382 strain was deposited at Russian National Collection of Industrial Microorganisms (VKPM) with a number VKPM B-7926 on Apr. 10, 2000, and the deposit was converted to an international deposit under the provisions of the Budapest Treaty on May 18, 2001.

Examples of *Serratia* bacteria which are able to produce L-arginine include *Serratia marcescens* which is unable to decompose L-arginine and is resistant to an arginine antagonist and canavanine, and is auxotorophic for lysine (see Japanese Patent Laid-open No. 52-8729).

Examples of coryneform bacteria which are able to produce L-histidine include microorganisms belonging to the genus *Brevibacterium* which are resistant to a thiamin antagonist, specifically, *Brevibacterium lactofermentum* FERM P-2170, FERM P-2316, FERM P-6478, FERM P-6479, FERM P-6480 and FERM P-6481 strains (Japanese Patent Laid-open Publication No. 59-63194). Furthermore, the examples include mutant strains belonging to the genus *Brevibacterium* or *Corynebacterium* which are resistant to polyketides and L-histidine producing ability, specifically, the FERM P-4161, FERM P-7273, FERM P-8371, FERM P-8372 and ATCC 14067 strains.

Examples of *Escherichia* bacteria which are able to produce L-histidine include mutant strains belonging to the genus *Escherichia* which are resistant to a histidine analogue, for example, the *E. coli* R-344 strain, and *Escherichia* bacteria transformed with L-histidine synthesis system enzyme genes isolated from the strain R-344. Specifically, the examples include the *E. coli* NRRL-12116, NRRL-12118, NRRL-12119, NRRL-12120 and NRRL-12121 strains (Japanese Patent Laid-open No. 56-5099).

Examples of *Bacillus* bacteria able to produce L-histidine include mutant strains belonging to the genus *Bacillus* which are resistant to a histidine analogue, and *Bacillus* bacteria transformed with a gene obtained from these mutant strains which are involved in resistance to histidine antagonist. Specifically, the examples include the FERM BP-218, FERM BP-224 and FERM BP-219 strains (Japanese Patent Laid-open No. 58-107192).

The fermentation broth or the processed product thereof containing the basic substance obtained by the present invention will contain carbonate ions or bicarbonate ions as counter anions for the dissociated basic substance. These carbonate ions or bicarbonate ions are emitted as carbon dioxide gas when the culture medium is heated or concentrated, or if the pH of the medium is lowered by adding a strong acid such as hydrochloric acid. The relative amount of the basic substance among the solid components in the fermentation broth is thus increased.

According to the present invention, by using bicarbonate ions, carbonate ions or the like in place of chloride ions and sulfate ions, the amount of the chloride ions can be reduced even to a level not causing corrosion of equipments, or sulfate ions can be reduced. Furthermore, after the fermentation, bicarbonate ions and carbonate ions can be replaced with chloride ions only by adding hydrochloric acid to the medium, lysine hydrochloride can be obtained only by further concentrating the medium without using ion exchange, and further, crystals of lysine hydrochloride can be directly separated.

In the present invention, the "fermentation product" includes concentrate and dried product obtained from the fermentation broth, and products obtained by processing the fermentation broth or dried product thereof.

EXAMPLES

Hereafter, the present invention will be explained more specifically with reference to the following examples.

Example 1

Construction of L-Lysine Producing Coryneform Bacterium

A gene coding for desensitized aspartokinase and a gene coding for a lysine secretion factor were introduced into a wild coryneform bacterium to prepare an L-lysine producing bacterium.

(1) Acquisition of Gene Coding for Desensitized Aspartokinase

A gene (lysC*) coding for aspartokinase (Ask*) which is desensitized to feedback inhibition by L-lysine and L-threonine was isolated by PCR from an L-lysine producing mutant strain, AJ3463 (FERM P-1987, see Japanese Patent Publication No. 51-34477) derived from the *Corynebacterium glutamicum* (*Brevibacterium lactofermentum*) ATCC 13869 strain by mutagenesis.

The AJ3463 strain was cultured in CM-Dex medium, and chromosomal DNA was extracted from the obtained cells by a typical method (Biochem. Biophys. Acta., 72, 619-629 (1963)). By using this chromosomal DNA as a template with an oligonucleotide ASK-F (SEQ ID NO: 1) for introducing a restriction enzyme BamHI site at the 5' end of the objective DNA fragment and an oligonucleotide ASK-R (SEQ ID NO: 2) for introducing a restriction enzyme KpnI site at the 3' end of the objective DNA fragment as primers for PCR, a gene DNA fragment containing lysC* as the objective gene was amplified. For amplification, a cycle consisting of a denaturation step at 98° C. for 10 seconds, an annealing step at 55° C. for 30 second and an extension step at 72° C. for 2 minutes was repeated 25 times. Enzyme, Pyrobest DNA Polymerase (Takara Shuzo), was used according to the manufacturer's instructions.

The amplified DNA fragment was purified by a phenol/chloroform treatment and ethanol precipitation, and then digested with the restriction enzymes BamHI and KpnI. The obtained reaction mixture was developed by agarose gel electrophoresis, the band containing the lysC* gene was excised, and the gene fragment was purified by conventional methods.

A shuttle vector for *E. coli* and *Corynebacterium glutamicum*, pVK7 (see U.S. Pat. No. 6,004,773), was separately treated with the restriction enzymes BamHI and KpnI in a similar manner, and ligated to the aforementioned lysC* fragment. Competent cells of the *E. coli* JM109 strain (Takara Shuzo) were transformed with the ligation reaction mixture according to the manufacturer's protocol, and several kanamycin-resistant colonies were selected.

The pVK7 was constructed by ligating a cryptic plasmid of *Brevibacterium lactofermentum*, pAM330, to a vector for *E. coli*, pHSG299 (Km$^r$, see Takeshita, S. et al., Gene, 61, 63-74, (1987)) as follows (see Japanese Patent Laid-open No. 11-266881, International Patent Publication WO99/07853). pAM330 was prepared from the *Brevibacterium lactofermentum* ATCC 13869 strain. pHSG299 was digested with AvaII (Takara Shuzo), which had been blunt-ended with T4 DNA polymerase, then digested with HindIII (Takara Shuzo), and ligated to pAM330 blunt-ended with T4 DNA polymerase. Thus, pVK7 was obtained. pVK7 is autonomously replicable in cells of *E. coli* and *Brevibacterium lactofermentum*, and contains a multiple cloning site derived from pHSG299, lacZ', and a kanamycin resistance gene as a marker.

Plasmid DNAs were extracted from the kanamycin-resistant colonies obtained as described above in a conventional manner, and the plasmid containing the objective lysC* gene was designated pVK-C*.

(2) Acquisition of a Gene Coding for Lysine Secretion Factor Lyse

By using chromosomal DNA from *Brevibacterium lactofermentum* ATCC 13869 as a template, the lysE gene was isolated by PCR (see U.S. Patent Application No. 2003113899). The lysE gene has been known to function in *Corynebacterium* bacteria to promote secretion of L-lysine (International Patent Publication 9723597A2). The chromosomal DNA of the strain was prepared in the same manner as described above.

LysE-F (SEQ ID NO: 3) and LysE-R (SEQ ID NO: 4) were used as the primers. The PCR was performed using Pyrobest (Takara Shuzo) with a heat treatment at 94° C. for 90 seconds, and the following cycle was repeated 30 times: denaturation at 94° C. for 20 seconds, annealing at 55° C. for 30 seconds and extension reaction at 72° C. for 60 seconds. Then the reaction was incubated at 72° C. for 10 minutes. A DNA fragment of the predicted size was obtained by this reaction. This DNA fragment was purified, and then cloned into cloning vector pCR2.1 (Invitrogene) according to the manufacturer's protocol. Competent cells of the *E. coli* JM109 strain (Takara Shuzo) were transformed with the ligation reaction mixture according to the manufacturer's protocol, and several ampicillin-resistant colonies were selected. Plasmid DNAs were extracted from these colonies, and the plasmid having the desired structure was designated pCRlysE.

Then, pCRlysE was digested with the restriction enzymes BamHI and XbaI, and subjected to agarose gel electrophoresis to obtain a fragment containing the lysE gene. A shuttle vector for *E. coli* and *Corynebacterium glutamicum*, pKC (see U.S. Patent application No. 2003113899), was separately treated with the restriction enzymes BamHI and KpnI in a similar manner, and subjected to agarose gel electrophoresis to obtain a gene fragment containing the chloramphenicol resistance gene. This gene was purified and then ligated to the aforementioned lysE fragment. By using this ligation reaction mixture, competent cells of the *E. coli* JM109 strain (Takara Shuzo) were transformed according to the manufacturer's protocol, and several chloramphenicol-resistant colonies were chosen. Plasmids were prepared from the colonies obtained as described above to obtain the LysE expression plasmid, plysE.

pKC4 was prepared as follows. A plasmid pHK4 (see Japanese Patent Laid-open No. 5-7491) having a replication origin derived from the already obtained plasmid pHM1519, which is autonomously replicable in coryneform bacteria (Agric. Biol. Chem., 48, 2901-2903 (1984)), was digested with the restriction enzymes BamHI and KpnI to obtain a gene fragment containing the replication origin. The obtained fragment was blunt-ended with a DNA Blunting Kit (Takara Shuzo), and inserted at the KpnI site of pHSG399 (Takara Shuzo) by ligation using a KpnI Linker (Takara Shuzo). Competent cells of the *E. coli* JM109 strain (Takara Shuzo) were transformed with this ligation reaction mixture according to the manufacturer's protocol, and several chloramphenicol-resistant colonies were selected. Plasmids were prepared from the colonies obtained as described above to obtain pKC4.

(3) Construction of L-Lysine Producing Coryneform Bacterium

The above-described two plasmids, pVK-C* and plysE, were introduced into the *Brevibacterium lactofermentum* ATCC 13869 strain by electroporation. The electroporation was performed by using Gene Pulser (BIO-RAD). The distance between the electrodes in the cuvette was 0.1 cm and the electric pulse application conditions were 25 μF, 200Ω and 1.8 kV. The strains containing the plasmids were selected on a CM-Dex agar plate (see below for the composition of the medium) containing 5 μg/l of chloramphenicol and 25 μg/l of kanamycin. The strain containing the plasmid was cultured overnight at 31.5° C. with shaking in the CM-Dex liquid medium containing 5 μg/l of chloramphenicol and 25 μg/l of kanamycin. The culture was performed in 3 ml of the culture medium in a test tube with shaking.

The CM-Dex medium was prepared as follows. All the components listed in Table 1 were mixed, adjusted to pH 7.5 with KOH, and then sterilized by autoclaving at 120° C. for 20 minutes. In the agar medium, agar was added to a final concentration of 20 g/L.

TABLE 1

| Composition of CM-Dex medium (per 1 L) | |
|---|---|
| Glucose | 5 g |
| Polypeptone | 10 g |
| Yeast extract | 10 g |
| KH$_2$PO$_4$ | 1 g |
| MgSO$_4$•7H$_2$O | 0.4 g |
| FeSO$_4$•7H$_2$O | 0.01 g |
| MnSO$_4$•4H$_2$O or 5H$_2$O | 0.01 g |
| Urea | 3 g |
| Mameno (soy bean protein hydrolysate, in terms of nitrogen weight) | 1.2 g |
| Biotin | 10 μg |

(Filled to 1 L with sterilized water)

As described above, an L-lysine producing coryneform bacterium, ATCC 13869/pVK-C*, plysE was obtained.

Example 2

Growth of L-Lysine Producing Bacterium in an Alkaline Medium, and Effect of the Total Ammonia Concentration on L-Lysine Production By using the L-lysine producing bacterium constructed in Example 1, the total ammonia concentration not inhibiting productivity of L-lysine in an alkaline medium was investigated.

First, a conventional culture method was used. That is, a medium (medium B) obtained by adding ammonium sulfate was added to the medium A (composition was shown in Table 2) in an amount of 55% (w/w) based on glucose was used. The pH of the medium was maintained constant with ammonia gas during the culture, to perform L-lysine fermentation. The pH was controlled to be 7.0 or 8.0.

TABLE 2

| Composition medium A (per 1 L) | |
|---|---|
| Glucose | 100 g |
| Yeast extract | 10 g |
| $KH_2PO_4$ | 1 g |
| $MgSO_4 \cdot 7H_2O$ | 1 g |
| Vitamin B1 hydrochloride | 2 mg |
| Biotin | 0.5 mg |
| Nicotinamide | 5 mg |
| $FeSO_4 \cdot 7H_2O$ | 10 mg |
| $MnSO_4 \cdot 4H_2O$ or $5H_2O$ | 10 mg |
| 10% GD-113 (antifoaming agent) | 0.05 mL |

Specifically, the culture was performed as follows. The aforementioned strain was inoculated into 3 ml of the CM-Dex liquid medium and cultured overnight at 31.5° C. with shaking, and 200 µl of the medium was uniformly spread onto CM-Dex agar medium. The culture was performed overnight at 31.5° C. as a stationary culture. Then, one third of the L-lysine producing bacterial cells which grew on the agar medium on one plate were inoculated to 300 ml of medium B in a jar fermenter and cultured. During the culture, the medium was aerated with 300 ml per minute of filter-sterilized air, the stifling rate was maintained at 700 rpm, and the temperature of the medium was maintained at 31.5° C. The results are shown in FIG. 1.

As a result, at pH 7.0, 17.4 g/L of L-lysine was accumulated, and the production rate was 0.725 g/L/hr. On the other hand, at pH 8.0, the growth of cells was almost not existent, and fermentation did not progress (FIG. 1).

Then, fermentation was performed using the L-lysine producing bacteria in a medium without ammonium sulfate.

The aforementioned strain was inoculated into 3 ml of the CM-Dex liquid medium and cultured overnight at 31.5° C. with shaking, and 200 µl of the medium was uniformly spread onto the CM-Dex agar medium and left overnight at 31.5° C. 300 ml of medium A (without ammonium sulfate) was placed in a jar fermenter, and the pH was adjusted to 7.8, 8.2, or 8.9 by bubbling ammonia gas through the medium. One third of the L-lysine producing bacterial cells which grew on the agar medium on one plate were inoculated into the medium, and cultured. During the culture, the medium was aerated with 300 ml per minute of filter-sterilized air, the stifling rate was maintained at 700 rpm, and the temperature of the medium was maintained constant at 31.5° C. During the culture, a constant pH was maintained by bubbling ammonia gas through the medium. As a result, it was confirmed that, at pH 8.9, after the total ammonia concentration in the medium exceeded 100 mM, growth and L-lysine production, in particular, were strongly inhibited.

In the aforementioned culture method, carbon dioxide gas generated by the L-lysine producing bacteria dissolved in the medium as carbonate ions or bicarbonate ions, which results in a lowered pH as the culture progresses. Therefore, the amount of added ammonia necessary to control the pH at the predetermined level increases. Furthermore, the pH level to which the medium had been adjusted became higher, the concentrations of dissolved carbonate ions and bicarbonate ions became higher, and therefore the concentration of the ammonia added in order to adjust the pH to the predetermined value became higher.

Non-dissociated ammonia easily penetrates cells resulting in cellular damage the cells. Since a higher pH results in a lower amount of dissociation of ammonia, the growth of bacteria was inhibited as the pH increases, even if the total ammonia concentration is maintained at a constant level. Therefore, it was concluded that at pH 8.9 or lower, if the total ammonia concentration is controlled to be low, for example, at 100 mM or lower, inhibition of bacterial growth and L-lysine accumulation is not significant.

Then, culture for L-lysine production was performed while the total ammonia concentration in the medium was controlled at 100 mM or lower at pH 7.8, 8.2, and 8.9.

The aforementioned strain was inoculated into 3 ml of the CM-Dex liquid medium and cultured overnight at 31.5° C. with shaking, and 200 µl of the medium was uniformly spread onto the CM-Dex agar medium and left overnight at 31.5° C. 300 ml of medium A (without ammonium sulfate) was placed in a jar fermenter, and the pH was adjusted to 7.5, 7.8, 8.2, or 8.9 by bubbling ammonia gas through the medium. One third of the L-lysine producing bacterial cells which grew on the agar medium on one plate were inoculated into the medium, and cultured. During the culture, the medium was aerated with 300 ml per minute of filter-sterilized air, the stirring rate was maintained at 700 rpm, and the temperature of the medium was maintained at 31.5° C. During the culture, the pH was maintained at each of the predetermined levels with 6 N potassium hydroxide instead of ammonia.

Figure 2:
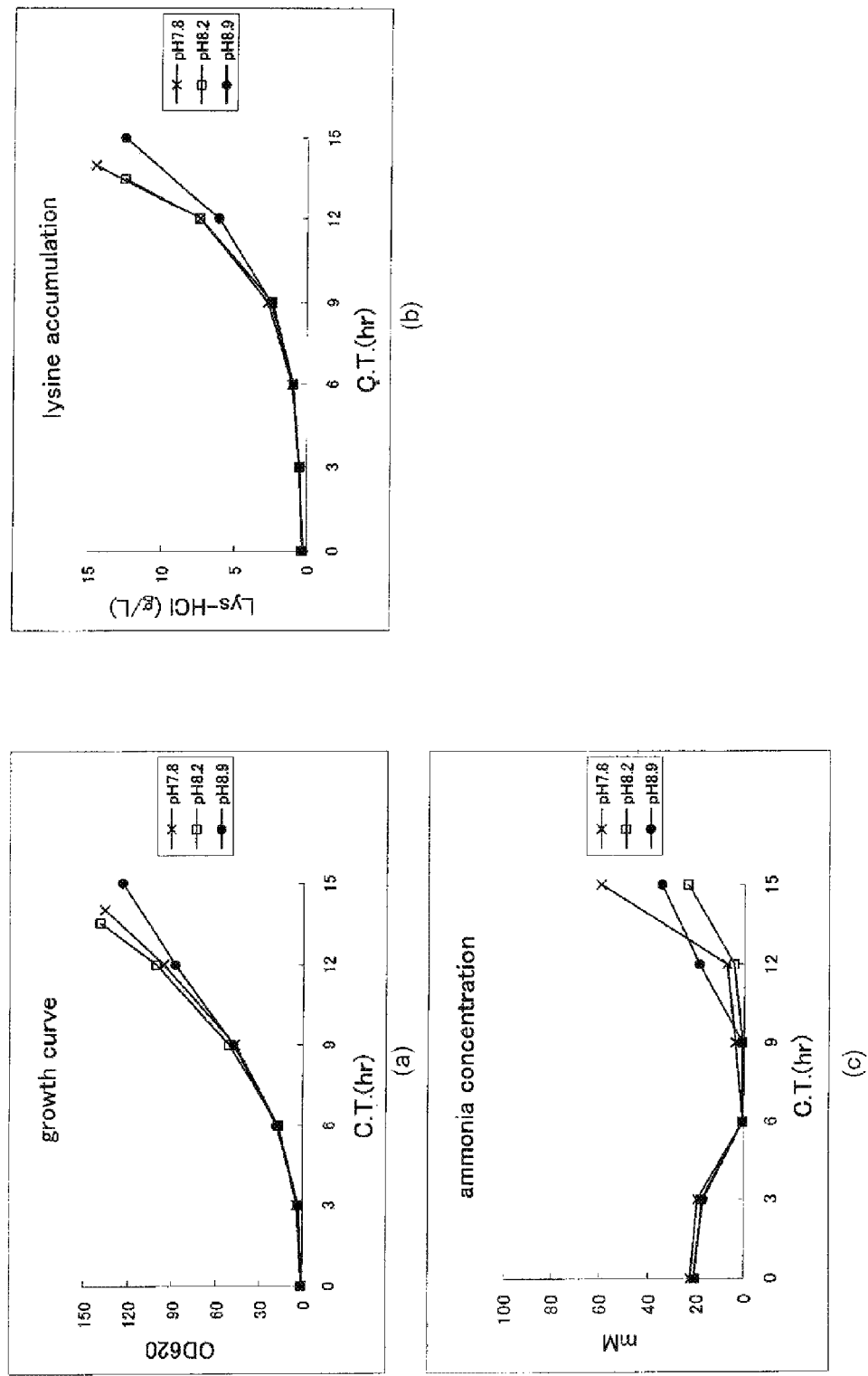
FIG. 2 shows the results of culture for L-lysine production performed in a medium with a limited ammonium concentration.

The total ammonia concentration in the medium was measured by using an ammonia electrode and an ion meter (Orion). The medium was periodically sampled, and the total ammonia concentration controlled to within 0 to 100 mM by adding 10% aqueous ammonia solution as required. Furthermore, by monitoring the dissolved oxygen concentration in the medium, a sharp increase in the dissolved oxygen concentration when ammonia was depleted was detected. When this occurred, a 10% aqueous ammonia solution was added to prevent continuous depletion of ammonia in the medium. The results are shown in FIG. 2.

As a result, favorable growth and L-lysine production were observed at all pH levels from 7.8 to 8.9. Compared with the fermentation performed at pH 7.0 using the conventional culture method, the production rate of 115% or higher was observed.

Example 3

Production of L-lysine

In this example, L-lysine fermentation was performed by controlling only the total ammonia concentration, but not controlling the pH. The range of the total ammonia concentration was maintained at 100 mM or lower. This range was chosen based on the results in Example 2.

Figure 3:
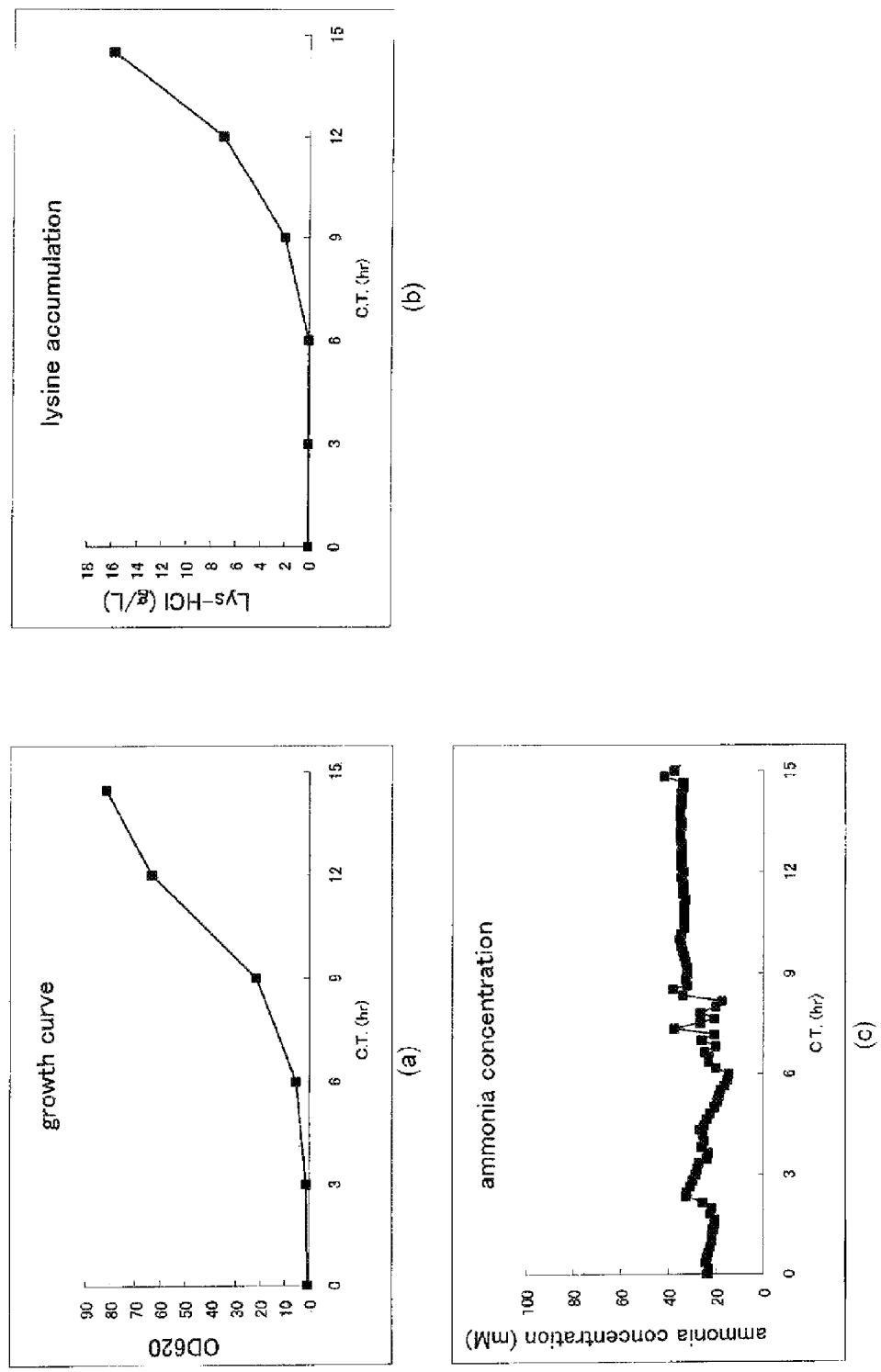
FIG. 3 shows the results of culture for L-lysine production performed by controlling only the total ammonia concentration and not controlling pH.

The aforementioned strain was inoculated into 3 ml of the CM-Dex liquid medium and cultured overnight at 31.5° C. with shaking, and 200 µl of the medium was uniformly spread onto the CM-Dex agar medium and left overnight at 31.5° C. 300 ml of medium A (without ammonium sulfate) was placed in a jar fermenter, and the total ammonia concentration of the medium was adjusted to 23.8 mM by bubbling ammonia gas through the medium. One third of the L-lysine producing bacterial cells which grew on the agar medium on one plate were inoculated into the medium, and cultured. During the culture, the medium was aerated with 300 ml per minute of filter-sterilized air, the stirring rate was maintained at 700 rpm, and the temperature of the medium was maintained at 31.5° C. The total ammonia concentration was measured periodically, and an appropriate amount of 10% aqueous ammonia was added to the medium as required so that the total ammonia concentration was maintained between 0 to 100 mM. As a result, 15.9 g/L of lysine was accumulated, and L-lysine fermentation progressed (FIG. 3).

Example 4

Construction of L-Lysine Producing *E. coli* Bacterium

<1> Construction of Strain in which the cadA and ldcC Genes Coding for Lysine Decarboxylase are Disrupted A lysine decarboxylase deficient strain was constructed first. Lysine decarboxylases are encoded by the cadA gene (Genbank Accession No. NP_418555, SEQ ID NO: 15), and the ldcC gene (Genbank Accession No. NP_414728, SEQ ID NO: 17) (see International Patent Publication WO96/17930). In this example, the WC196 strain was used as the parent strain.

The cadA and ldcC genes coding for lysine decarboxylase deleted by using the method developed first by Datsenko and Wanner called "Red-driven integration" (Proc. Natl. Acad. Sci. USA, 2000, vol. 97, No. 12, pp. 6640-6645), and an excision system derived from λ phage (J. Bacteriol., 2002 September, 184 (18):5200-3, Interactions between integrase and excisionase in the phage lambda excisive nucleoprotein complex, Cho EH, Gumport RI, Gardner JF). According to the "Red-driven integration" method, a PCR product obtained using synthetic oligonucleotide primers in which a part of the objective gene is designed on the 5' side and a part of an antibiotic resistance gene is designed on the 3' side, can be used to obtain a gene-disrupted strain in one step. Furthermore, by using the excision system derived from λ phage in combination, the antibiotic resistance gene which had been incorporated into the gene-disruption strain can be eliminated (Japanese Patent Laid-open No. 2005-058227).

(1) Disruption of the cadA Gene

The plasmid pMW118-attL-Cm-attR (Japanese Patent Laid-open No. 2005-058827) was used as a template in PCR. pMW118-attL-Cm-attR was obtained by inserting the attL and attR genes which are the attachment sites of λ phage, and the cat gene which is an antibiotic resistance gene into pMW118 (Takara Bio). The order of insertion is attL-cat-attR.

PCR was performed with the synthetic oligonucleotide primers shown as SEQ ID NOS: 11 and 12 which have sequences corresponding to both ends of attL and attR at the 3' ends of the primers, and a sequence corresponding to a portion of the objective cadA gene at the 5' ends of the primers.

The amplified PCR product was purified on agarose gel and introduced by electroporation into the *E. coli* WC169 strain which contains plasmid pKD46 which is temperature sensitive replicable. The plasmid pKD46 (Proc. Natl. Acad. Sci. USA, 2000, vol. 97, No. 12, pp. 6640-6645) contains a DNA fragment of 2154 nucleotides in total of λ phage containing genes coding for Red recombinase of the λ Red homologous recombination system (λ, β, exo genes) controlled by arabinose-inducible ParaB promoter (GenBank/EMBL Accession No. J02459, nucleotides at positions 31088 to 33241). The plasmid pKD46 is required to incorporate the PCR product into the chromosome of the WC196 strain.

Competent cells for the electroporation were prepared as follows. That is, the *E. coli* WC196 strain cultured overnight at 30° C. in the LB medium containing 100 mg/L of ampicillin was diluted 100 times with 5 mL of the SOB medium (Molecular Cloning: A Laboratory Manual, 2nd Edition, Sambrook, J. et al., Cold Spring Harbor Laboratory Press (1989)) containing ampicillin (20 mg/L) and L-arabinose (1 mM). The cells in the diluted culture were grown at 30° C. with aeration until the OD600 reached about 0.6, and then the culture was concentrated 100 times and washed three times with 10% glycerol so that the cells could be used for electroporation. The electroporation was performed by using 70 µl of the competent cells and about 100 ng of the PCR product. After the electroporation, the cells were added to 1 mL of the SOC medium (Molecular Cloning: A Laboratory Manual, 2nd Edition, Sambrook, J. et al., Cold Spring Harbor Laboratory Press (1989)), cultured at 37° C. for 2.5 hours, and then cultured at 37° C. as plate culture on L agar medium containing 25 mg/L of Cm (chloramphenicol), and Cm-resistant recombinants were selected. Then, in order to remove the pKD46 plasmid, the cells were subcultured twice at 42° C. on the L agar medium containing Cm, and ampicillin resistance of the colonies was examined to obtain an ampicillin-sensitive strain without pKD46.

Deletion of the cadA gene in the mutant identified on the basis of the chloramphenicol resistance gene was confirmed by PCR. The obtained cadA deficient strain was designated WC196ΔcadA::att-cat strain.

Then, in order to remove the att-cat gene which had been introduced into the cadA gene, a helper plasmid pMW-intxis-ts (Japanese Patent Laid-open No. 2005-058827) was used. pMW-intxis-ts carries a gene coding for integrase (Int) and a gene coding for excisionase (Xis) of λ phage, and is temperature sensitive replicable.

Competent cells of the WC196ΔcadA::att-cat strain obtained above were prepared in a conventional manner, transformed with the helper plasmid pMW-intxis-ts, and cultured on L-agar medium containing 50 mg/L of ampicillin at 30° C. as a plate culture, and ampicillin-resistant strains were selected.

Then, in order to remove the pMW-intxis-ts plasmid, the selected strains were subcultured twice on L-agar medium at 42° C., and ampicillin resistance and chloramphenicol resistance of the obtained colonies were examined to obtain a chloramphenicol- and ampicillin-sensitive cadA-disrupted strain without att-cat and pMW-intxis-ts. This strain was designated WC196ΔcadA.

(2) Deletion of the ldcC Gene from the WC196ΔcadA Strain

The ldcC gene was deleted from the WC196ΔcadA strain according to the aforementioned method using the primers of SEQ ID NOS: 13 and 14 as primers for disruption of ldcC. A cadA- and ldcC-disrupted strain, WC196ΔcadAΔldcC, was thereby obtained.

<2> Introduction of Plasmid for Lys Production into WC196ΔcadAΔldcC Strain

The WC196ΔcadAΔldcC strain was transformed with plasmid pCABD2 for Lys production carrying the dapA, dapB and lysC genes (International Patent Publication WO01/53459) in a conventional manner to obtain WC196ΔcadAΔldcC/pCABD2 strain (WC196LC/pCABD2).

Example 5

L-Lysine Production Using *E. coli*

This example shows an example of the present invention applied to the production of L-lysine by *E. coli*. In this example, L-lysine was produced by fermentation without adding ammonium sulfate and ammonium chloride, which are generally added to the media for the purpose of supplying nitrogen and counter ions for L-lysine in L-lysine production by fermentation. Specifically, the culture was performed without controlling the pH, but controlling the ammonia concentration in the medium. The range within which the ammonia concentration in the medium should be controlled was examined beforehand. As a result, it was confirmed that the total ammonia concentration is preferably in the range of 50 to 100 mM. Therefore, in the practical main culture, the total ammonia concentration was controlled to be 100 mM or lower by bubbling ammonia gas. Furthermore, when the total ammonia concentration decreased to 50 mM, it was controlled with ammonia gas to maintain that concentration.

WC196ΔcadAΔldcC/pCABD2 was used for lysine production. 300 ml of the L-lysine production medium for *E. coli* shown in Table 3 placed in a jar fermenter was used. The total ammonia concentration was adjusted to 95 mM by bubbling ammonia gas To this medium, cells obtained by culturing the L-lysine producing strain on the entire surface of LB agar medium containing 20 μg/L of streptomycin and culturing it at 37° C. for 24 hours were inoculated. The amount of the inoculated cells corresponded to the cells grown on three plates of the agar medium. The culture was performed with a temperature of the medium maintained at 37° C., aeration of 50 ml per minute of filter-sterilized air, and a stirring rate of 700 rpm. When the dissolved oxygen concentration in the medium decreased to 20% saturation, the aeration rate was changed to 100 mL per minute. The feed solution for *E. coli* shown in Table 4 was appropriately added dropwise to the medium so that glucose is not depleted, and the concentration thereof does not become 30 g/L or higher in the medium. Finally, when 36 g of glucose was consumed, the culture was terminated. As a result, the culture could be favorably performed so that all the added glucose was consumed after 33 hours, 13.4 g of L-lysine was accumulated, and the production rate of L-lysine was 1.2 g/L/hr. The yield of this production was 37%.

As a control, results are shown for L-lysine production performed with the same strain by adding ammonium sulfate, and not controlling the total ammonia concentration, but controlling the pH, similar to common production methods for basic amino acids. The same strain was inoculated in a similar manner to a medium consisting of the L-lysine production medium for *E. coli* shown in Table 3 added with 13 g/L of ammonium sulfate, and cultured while controlling the pH to be constant at 6.7 by appropriately bubbling ammonia gas. The culture temperature, aeration rate, and stirring rate were the same as those described above. In this case, the feed solution for *E. coli* added with 112.5 g/L of ammonium sulfate (containing ammonium sulfate, Table 5) was added instead of the feed solution for *E. coli* shown in Table 4, so that that glucose is not depleted, and glucose concentration should not become 30 g/L or higher in the medium, and finally 36 g of glucose was consumed. As a result, all the added glucose was consumed after 33 hours, 14.7 g of L-lysine was accumulated, and the production rate of L-lysine was 1.3 g/L/hr. The yield of this production was 40%.

Figure 4:
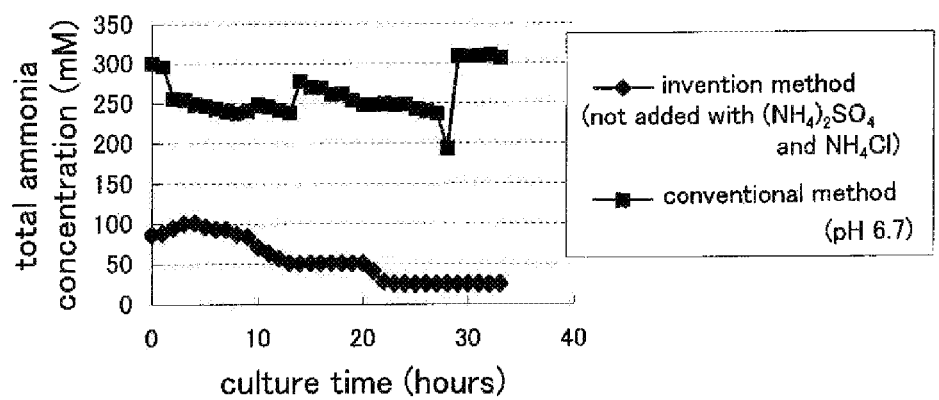
FIG. 4 shows changes in total ammonia concentration (4a) and pH (4b) over time in a conventional medium and a medium without ammonium sulfate and ammonium chloride.
Figure 4:
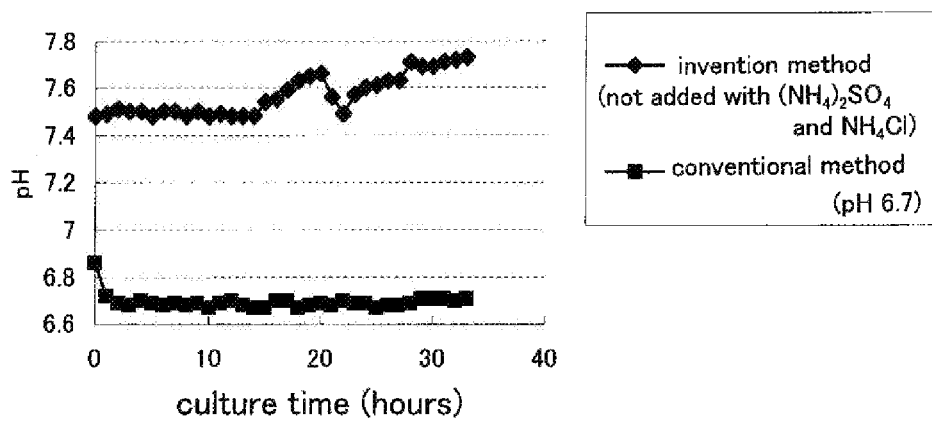
Figure 5:
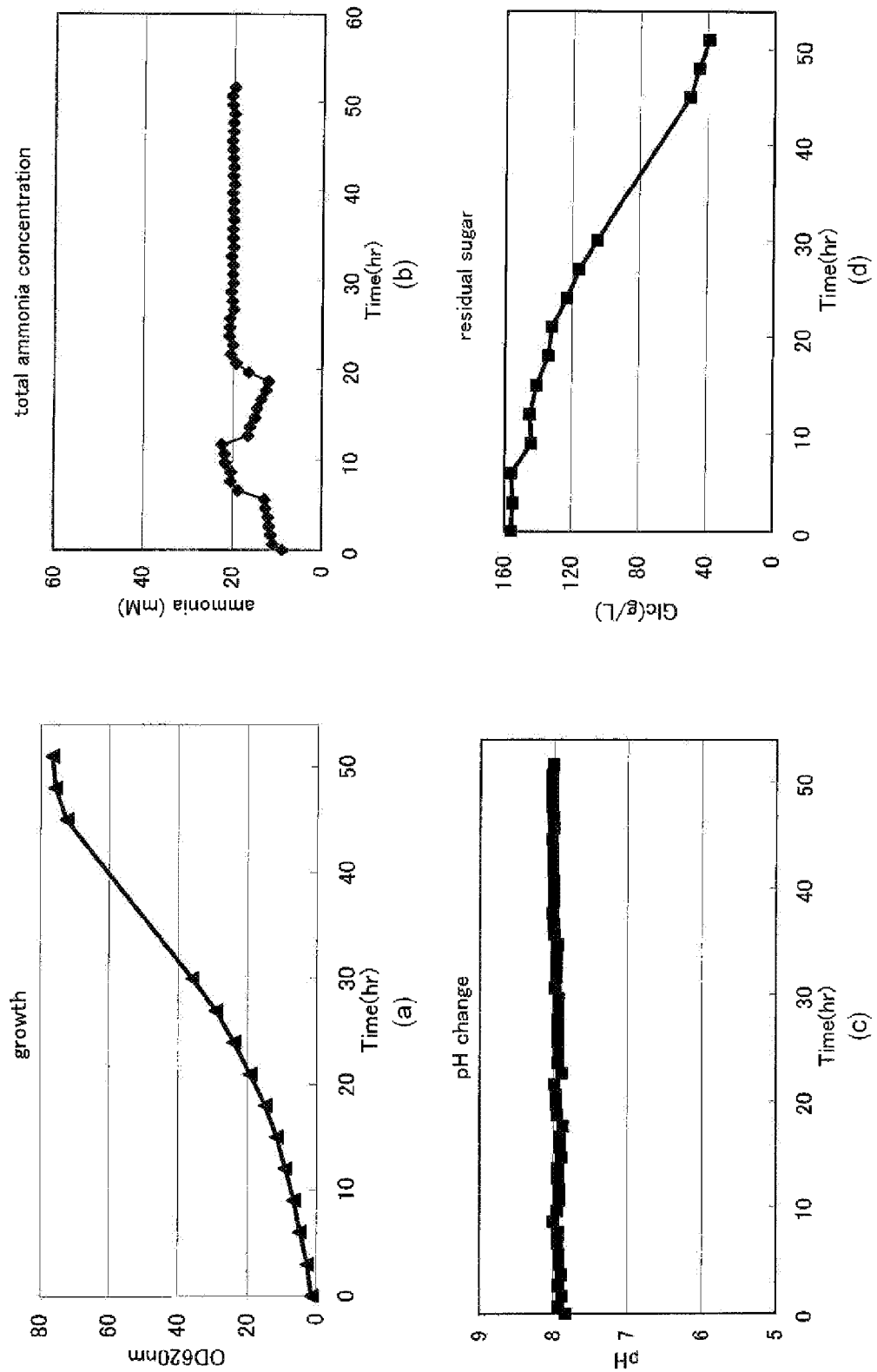
FIG. 5 shows the changes in growth (5a), total ammonia concentration (5b), pH (5c), and remaining sugar amount (5d) over time in L-arginine fermentation in a medium with a limited ammonium concentration.
Figure 6:
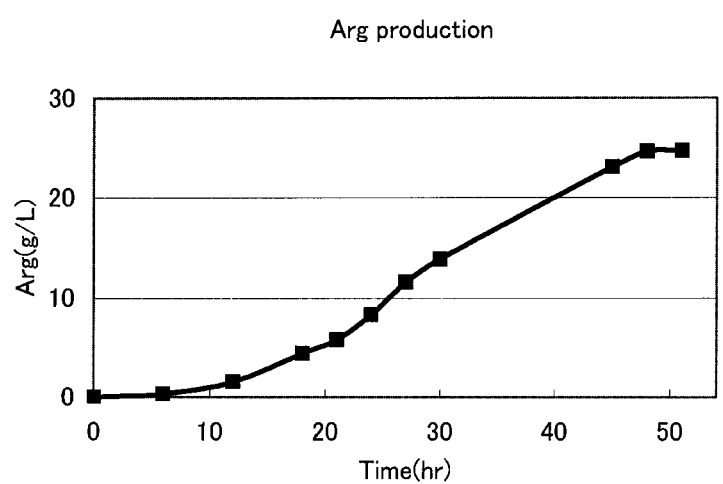
FIG. 6 shows the results of a culture for L-arginine production in a medium with a limited ammonium concentration.

All the lysine concentrations described above are shown in terms of lysine hydrochloride. Furthermore, changes in the total ammonia concentration and pH during the cultures are shown in FIG. 4. From comparison of these results, it was confirmed that, when the method of the present invention was used, L-lysine production by fermentation could be performed without adding ammonium sulfate or ammonium chloride at a production rate of about 92%, a yield of about 93% and an L-lysine production amount of about 91% compared with those obtained in the common fermentative production in which ammonium sulfate was added.

TABLE 3

Composition of L-lysine production medium for *E. coli* (per 1 L)

| | |
|---|---|
| glucose | 30 g |
| KH$_2$PO$_4$ | 1 g |
| MgSO$_4$•7H$_2$O | 1.2 g |
| Mameno (soy bean protein hydrolysate, in terms of nitrogen weight) | 0.77 g |
| FeSO$_4$•7H$_2$O | 30 mg |
| MnSO$_4$•4H$_2$O or 5H$_2$O | 30 mg |
| p-aminobenzoic acid | 2 mg |
| L-threonine | 300 mg |
| DL-methionine | 200 mg |
| cystine | 150 mg |
| betaine | 3.5 g |
| GD-113 (antifoaming agent) | 0.05 mL |

Glucose and FeSO$_4$.7H$_2$O were weighed as a portion A, the other components were weighed as a portion B, and the portion A as it was and the portion B adjusted to pH 5.0 were separately sterilized by autoclaving at 115° C. for 10 minutes, and then mixed. 20 μg/L of streptomycin was added to the medium prior to use.

TABLE 4

Composition of feed solution for *E. coli* (per 1 L)

| | |
|---|---|
| glucose | 561 g |
| GD-113 | 7 μl |
| KH$_2$PO$_4$ | 1.48 g |
| L-thr | 0.44 g |

The components were sterilized by autoclaving at 120° C. for 20 minutes.

20 μg/L of streptomycin was added to the medium prior to use.

TABLE 5

Composition of feed solution for *E. coli* containing ammonium sulfate (per 1 L)

| | |
|---|---|
| glucose | 561 g |
| GD-113 | 7 μl |
| KH$_2$PO$_4$ | 1.48 g |
| L-thr | 0.44 g |
| (NH$_4$)$_2$SO$_4$ | 112.5 g/L |

The components were sterilized by autoclaving at 120° C. for 20 minutes.

20 μg/L of streptomycin was added to the medium prior to use.

Example 6

Production of L-Arginine

This example shows an example of the present invention applied to L-arginine production by a coryneform bacterium. *Corynebacterium glutamicum* AJ12092 (FERM BP-6906) was used as the L-arginine-producing strain.

First, as a control, results are shown for L-arginine production performed with the same strain by adding ammonium sulfate, and not controlling the total ammonia concentration, but controlling the pH, similar to a common methods for production of a basic amino acid. A medium for L-arginine production having the composition shown in Table 6, with the addition of 65 g/L of ammonium sulfate, Also, the glucose concentration was changed to 40 g/L. 300 ml of this medium was placed in a jar fermenter, and the pH was controlled to be 7.0 by bubbling ammonia gas. To this medium, two plates of cells obtained by culturing the *Corynebacterium glutamicum* AJ12092 strain on the entire surface of CM-Dex agar medium at 31.5° C. for 24 hours were inoculated. The culture was performed at a temperature of the medium maintained at 31.5° C. with aeration of 150 ml per minute of filter-sterilized air and stifling at a rate of 700 rpm. Furthermore, during the culture, the pH was controlled to be 6.9 by adding a 6 N KOH solution which had been separately sterilized. As the culture progresses, the glucose concentration decreases. In order to maintain the glucose concentration at 30 to 40 g/L, a separately sterilized glucose solution of 692 g/L was appropriately added. The culture was performed for 54 hours. As a result, 23.4 g/L of L-arginine was accumulated, the production yield of L-arginine was 26.7% of the consumed glucose, and the production rate was 0.43 g/L/hr. The amount of glucose consumed during the culture was 29.1 g per batch.

Production of L-arginine when ammonium sulfate is not added to the medium, and while controlling only the total ammonia concentration, but not the pH was performed. The results are shown hereinafter. 300 ml of the L-arginine production medium having the composition shown in Table 6 but not containing ammonium sulfate was placed in a jar fermenter, and the total ammonia concentration was adjusted to 12.6 mM by bubbling ammonia gas. To this medium, two plates of cells of the L-arginine producing strain cultured in the same manner as that of the control were inoculated. The culture was performed in the same manner as that of the control with maintaining the temperature at 31.5° C., aerating 150 ml per minute of filter-sterilized air, and maintaining the stirring rate at 700 rpm. By measuring the total ammonia concentration of the medium periodically or using an ammonia concentration controlling apparatus, the total ammonia in the medium was controlled so that it was at various levels during the culture. As a result, it was confirmed that the total ammonia concentration in the medium controlled to be about 20 mM by adding ammonia gas as required provided favorable results. The culture performed with controlling the total ammonia concentration in the medium to be about 20 mM based on the above result favorably progressed, 24.2 g/L of L-arginine was accumulated after 51 hours, and thus L-arginine fermentation was attained (FIG. 4). The glucose consumed during the culture was 35.1 g per batch, the production yield of L-arginine was 20.6% of the consumed glucose, and the production rate was 0.47 g/L/hr. Furthermore, the pH of the medium increased from 7.92 at the start of the culture to 8.02 at the end of the culture.

From the comparison of these results with those of the control experiment, it was demonstrated that the L-arginine production by fermentation could be performed without adding ammonium sulfate or ammonium chloride at a yield of about 77% and a production rate higher by about 9% compared with those obtained in the common fermentative production in which ammonium sulfate was added.

TABLE 6

| Composition of L-arginine production medium (per 1 L) | |
|---|---|
| glucose | 150 g |
| $KH_2PO_4$ | 1 g |
| $MgSO_4 \cdot 7H_2O$ | 0.4 g |
| Mameno (soy bean protein hydrolysate, in terms of nitrogen weight) | 0.23 g |
| vitamin B1 hydrochloride | 0.5 mg |
| biotin | 0.5 mg |
| $FeSO_4 \cdot 7H_2O$ | 10 mg |
| $MnSO_4 \cdot 4H_2O$ or $5H_2O$ | 10 mg |
| GD-113 (antifoaming agent) | 0.05 mL |

The medium was adjusted to pH 7.0 with potassium hydroxide aqueous solution, up to 1 L, and sterilized by autoclaving at 115° C. for 10 minutes.

EXPLANATION OF SEQUENCE LISTING

SEQ ID NO: 1: Primer sequence for cloning of lysC gene
SEQ ID NO: 2: Primer sequence for cloning of lysC gene
SEQ ID NO: 3: Primer sequence for cloning of lysE gene
SEQ ID NO: 4: Primer sequence for cloning of lysE gene
SEQ ID NO: 5: Nucleotide sequence of lycC* gene and amino acid sequence of α-subunit of inhibition-desensitized aspartokinase
SEQ ID NO: 6: Amino acid sequence of α-subunit of inhibition-desensitized aspartokinase
SEQ ID NO: 7: Nucleotide sequence of lycC* gene and amino acid sequence of β-subunit of inhibition-desensitized aspartokinase
SEQ ID NO: 8: Amino acid sequence of β-subunit of inhibition-desensitized aspartokinase
SEQ ID NO: 9: Nucleotide sequence of lysE gene and amino acid sequence of LysE protein
SEQ ID NO: 10: Amino acid sequence of LysE protein
SEQ ID NO: 11: Primer for disruption of cadA gene
SEQ ID NO: 12: Primer for disruption of cadA gene
SEQ ID NO: 13: Primer for disruption of ldc gene
SEQ ID NO: 14: Primer for disruption of ldc gene
SEQ ID NO: 15: Nucleotide sequence of cadA gene and amino acid sequence of lysine decarboxylase
SEQ ID NO: 16: Amino acid sequence of lysine decarboxylase (cadA)
SEQ ID NO: 17: Nucleotide sequence of ldc gene and amino acid sequence of lysine decarboxylase
SEQ ID NO: 16: Amino acid sequence of lysine decarboxylase (ldc)

INDUSTRIAL APPLICABILITY

According to the present invention, a basic substance can be produced by fermentation even at a high pH, which enables reduction of the amounts of industrial raw materials such as ammonium sulfate, without substantially degrading the performances essentially obtained in the conventional common culture methods such as productivity.

Although the fermentation broth obtained by the method of the present invention contains carbonate ions and/or bicarbonate ions, these are easily emitted into air by heating, and therefore a fermentation broth or fermentation product with a large amount of the basic substance present as a solid can be obtained. Furthermore, when purification is needed, if an acid stronger than carbonic acid is added to the fermentation broth, carbonate can be easily replaced with the stronger acid without performing ion exchange, which is usually performed in the conventional production methods. Furthermore, crystals of lysine hydrochloride can be directly obtained by concentrating the fermentation broth.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing a basic amino acid, the method comprising:
culturing a bacterium having an ability to produce a basic amino acid in a liquid medium in a fermentation tank to produce and accumulate the basic amino acid in the medium, wherein the amount of sulfate and/or chloride ions which function as counter ions of the basic amino acid is reduced by adjusting the total ammonia concentration in the medium to be 200 mM or lower during a period when the pH of the medium increases due to a shortage of the counter ions caused by accumulation of the basic amino acid.

2. The method according to claim 1, wherein the bacterium is a coryneform bacterium or an *Escherichia* bacterium.

3. The method according to claim 1, wherein the bacterium is *Escherichia coli*.

4. The method according to claim 1, further comprising: heating the medium or a processed product thereof after the culturing to eliminate bicarbonate ions and carbonate ions.

5. The method according to claim 1, wherein the basic amino acid is L-lysine.

6. The method according to claim 1, wherein the basic amino acid is L-arginine.

7. The method according to claim 5, wherein the bacterium belongs to the genus *Corynebacterium*, and wherein the bacterium has been modified so that the expression of lysE gene is enhanced.

8. The method according to claim 7, wherein the lysE gene is selected from the group consisting of:
(a) a DNA comprising the nucleotide sequence of nucleotides 1025 to 1723 in SEQ ID NO: 9, and
(b) a DNA which is able to hybridize with a sequence complementary to the nucleotide sequence of nucleotides 1025 to 1723 in SEQ ID NO: 9 under stringent conditions comprising washing at 60° C., 0.1×SSC, 0.1% SDS.

9. The method according to claim 5, wherein the bacterium is *Escherichia coli*, and wherein the bacterium has been modified so that activity of lysine decarboxylase is decreased.

10. The method according to claim 5, wherein the bacterium is *Escherichia coli*, and wherein the bacterium has aspartokinase which is desensitized to feedback inhibition by L-lysine and L-threonine.

11. The method according to claim 1, wherein a saccharide, an alcohol, or a hydrocarbon is used as the carbon source.

12. The method according to claim 1, wherein the total ammonia concentration in the medium is adjusted by adding ammonia or urea to the medium when an activity of the bacterium is reduced or ceases as determined based on the indicators: dissolved oxygen concentration in the medium, consumption rate of carbon source in the medium, turbidity of the medium, productivity of the basic amino acid, and pH change in the medium.

13. The method according to claim 1, wherein a medium having the same composition as that of a medium containing sulfate ions and/or chloride ions as a counter ion source of the basic amino acid in an amount sufficient for performing the culture at pH 7.2 or lower except that amount of sulfate ions and/or chloride ions is reduced by a desired amount is used as the medium, and wherein the period is a period where the pH of the medium cannot be maintained to be 7.2 or lower due to a shortage of counter ions for the basic amino acid which has accumulated in the medium.

* * * * *